United States Patent
Zhu et al.

(10) Patent No.: US 11,524,957 B2
(45) Date of Patent: Dec. 13, 2022

(54) PROCESS FOR THE SYNTHESIS OF 2-[(2S)-1-AZABICYCLO[2.2.2]OCT-2-YL]-6-(3-METHYL-1H-PYRAZOL-4-YL)THIENO[3,2-D]PYRIMIDIN-4(3H)-ONE

(71) Applicant: TAKEDA PHARMACEUTICAL COMPANY LIMITED, Osaka (JP)

(72) Inventors: Lei Zhu, Bedford, MA (US); John Daniel Bailey, Cambridge, MA (US); Landon Durak, Cambridge, MA (US); Joshua David Waetzig, Waltham, MA (US); Masahiro Mizuno, Osaka (JP); Kazuhiro Maeda, Osaka (JP); Tsuneo Yasuma, Osaka (JP); Hiroshi Yamaguchi, Osaka (JP); Koichiro Fukuoka, Osaka (JP); Kazuyuki Akiyama, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 17/044,366

(22) PCT Filed: Apr. 1, 2019

(86) PCT No.: PCT/JP2019/015237
§ 371 (c)(1),
(2) Date: Oct. 1, 2020

(87) PCT Pub. No.: WO2019/194319
PCT Pub. Date: Oct. 10, 2019

(65) Prior Publication Data
US 2021/0101897 A1    Apr. 8, 2021

Related U.S. Application Data

(60) Provisional application No. 62/651,494, filed on Apr. 2, 2018.

(51) Int. Cl.
*C07D 453/02*    (2006.01)
*C07D 409/04*    (2006.01)

(52) U.S. Cl.
CPC ......... *C07D 453/02* (2013.01); *C07D 409/04* (2013.01)

(58) Field of Classification Search
CPC ............................ C07D 453/02; C07D 409/04
See application file for complete search history.

(56) References Cited

U.S. PATENT DOCUMENTS 8,722,660 B2 *    5/2014    Homma ............... A61K 31/541
514/210.21

* cited by examiner

*Primary Examiner* — Rebecca L Anderson
(74) *Attorney, Agent, or Firm* — Honigman LLP; Lucy X. Yang; Jonathan P. O'Brien

(57) ABSTRACT

The present invention provides processes and synthetic intermediates for the synthesis of 2-[(2S)-1-azabicyclo[2.2.2]oct-2-yl]-6-(3-methyl-1H-pyrazol-4-yl)thieno[3,2-d]pyrimidin-4{3H)-one or a salt, hydrate, or tautomer thereof, or any combination thereof, which are Cdc7 kinase inhibitors, and are useful for the treatment of disorders of cell proliferation, particularly cancer, and other disorders associated with Cdc7 activity.

12 Claims, 1 Drawing Sheet

Summary of dynamic resolution study using (+)DBTA·H₂O
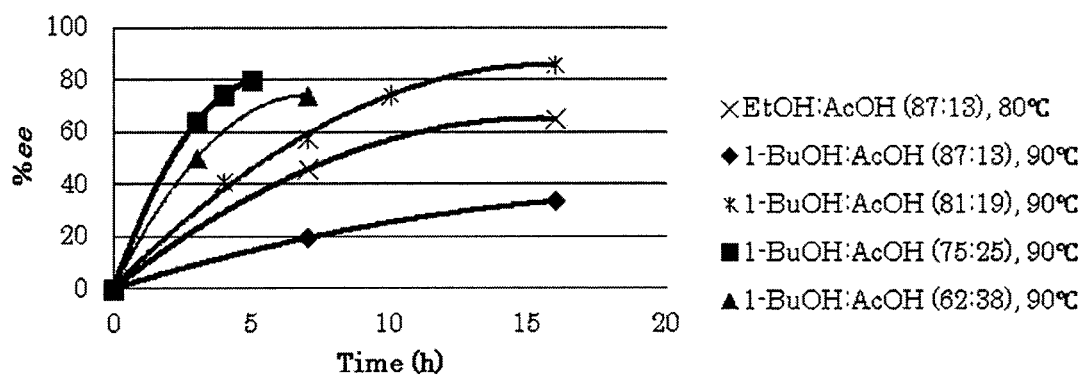

PROCESS FOR THE SYNTHESIS OF 2-[(2S)-1-AZABICYCLO[2.2.2]OCT-2-YL]-6-(3-METHYL-1H-PYRAZOL-4-YL)THIENO[3,2-D]PYRIMIDIN-4(3H)-ONE

CROSS-REFERENCE TO RELATED APPLICATIONS

This application is a 35 U.S.C. § 371 United States National Phase Application of, and claims priority to, PCT Application No. PCT/JP2019/015237, filed Apr. 1, 2019, which claims the priority benefit of U.S. Provisional Patent Application No. 62/651,494, filed Apr. 2, 2018.

FIELD OF THE INVENTION

The present invention relates to processes for the synthesis of the compound 2-[(2S)-1-azabicyclo[2.2.2]oct-2-yl]-6-(3-methyl-1H-pyrazol-4-yl)thieno[3,2-d]pyrimidin-4(3H)-one (Compound XI) or a salt, hydrate, or tautomer thereof, or any combination thereof, wherein Compound (XI) has the structure:

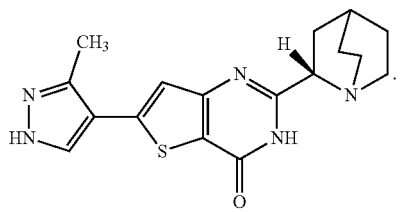

(XI)

BACKGROUND OF THE INVENTION

U.S. Pat. No. 8,722,660 $B_2$ discloses compounds that are effective inhibitors of Cdc7. The compounds are useful for inhibiting Cdc7 kinase activity in vitro and in vivo and are useful for the treatment of disorders of cell proliferation, particularly cancer.

U.S. Pat. No. 8,722,660 $B_2$ additionally discloses pharmaceutical compositions containing these compounds, and methods for the treatment or therapy of diseases, disorders, or conditions associated with Cdc7 kinase, including proliferative diseases such as cancer.

PCT publication WO2017/172565 discloses crystalline forms of compound 2-[(2S)-1-azabicyclo[2.2.2]oct-2-yl]-6-(3-methyl-1H-pyrazol-4-yl)thieno[3,2-d]pyrimidin-4(3H)-one hemihydrate and/or tautomers thereof.

Efficient chemical synthesis of Compound XI is challenging due to its chiral center which is easily epimerized under acidic and basic conditions. Therefore, a chiral induction or chiral resolution at the upper stream is not effective. Chiral column chromatography resolution or diastereomeric salt resolution methods of resolving the racemic compound are generally used to obtain the chiral compound, but result in significant waste. Thus, there is a strong need for more efficient chemical process for the preparation of Compound XI.

SUMMARY OF THE INVENTION

In one aspect, described herein is a process for preparing a compound, which is 2-[(2S)-1-azabicyclo[2.2.2]oct-2-yl]-6-(3-methyl-1H-pyrazol-4-yl)thieno[3,2-d]pyrimidin-4(3H)-one, represented as Compound (XI):

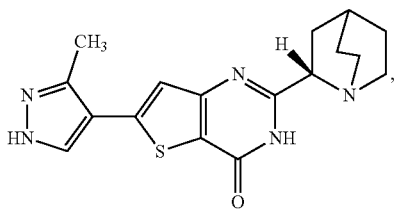

(XI)

or a salt, hydrate, or tautomer thereof, or any combination thereof, the process comprising converting a chiral center of 2-(1-azabicyclo[2.2.2]oct-2-yl)-6-(3-methyl-1H-pyrazol-4-yl)thieno[3,2-d]pyrimidin-4(3H)-one, represented as Compound (VIII):

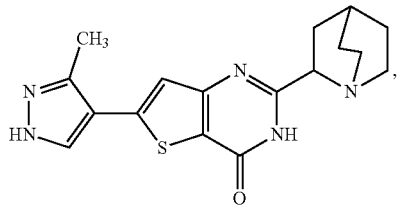

(VIII)

or a salt, hydrate, or tautomer thereof, or any combination thereof, to form the Compound (XI) or salt, hydrate, or tautomer thereof, or combination thereof.

In another aspect, described herein is a process for preparing a compound, which is 2-(1-azabicyclo[2.2.2]oct-2-yl)-6-[1-(4-methoxybenzyl)-5-methyl-1H-pyrazol-4-yl]thieno[3,2-d]pyrimidin-4(3H)-one, represented as Compound (VI):

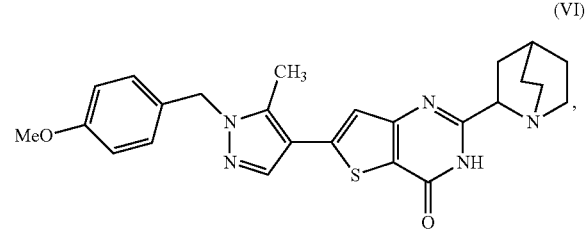 [SMILES: COc1ccc(Cn2ncc(-c3cc4nc(C5CC6CCN5CC6)[nH]c(=O)c4s3)c2C)cc1]

(VI)

or a salt, hydrate, or tautomer thereof, or any combination thereof, the process comprising: treating a compound, which is methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate, represented as Compound (V):

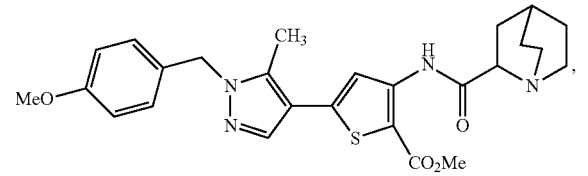

(V)

or a salt, hydrate, or tautomer thereof, or any combination thereof, with a mixture comprising formamide and a base to form the Compound (VI) or salt, hydrate, or tautomer thereof, or combination thereof.

In another aspect, described herein is a process for preparing a compound, which is 2-(1-azabicyclo[2.2.2]oct-2- yl)-6-(3-methyl-1H-pyrazol-4-yl)thieno[3,2-d]pyrimidin-4(3H)-one dihydrochloride, represented as Compound (VII):

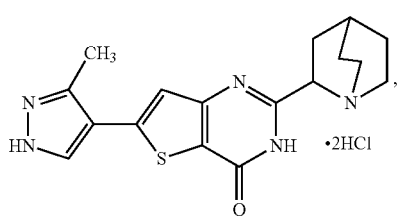

(VII)

or a hydrate or tautomer thereof, or any combination thereof, wherein the process comprises:
deprotecting a compound represented as Compound (XXI):

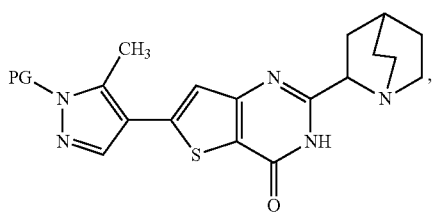

(XXI)

or a salt, hydrate, or tautomer thereof, or any combination thereof in a first reaction mixture, wherein PG is an amine protecting group, to form the 2-(1-azabicyclo[2.2.2]oct-2-yl)-6-(3-methyl-1H-pyrazol-4-yl)thieno[3,2-d]pyrimidin-4(3H)-one, represented as Compound (VIII):

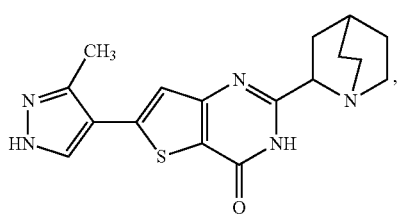

(VIII)

or a salt, hydrate, or tautomer thereof, or any combination thereof; and
treating the first reaction mixture with hydrogen chloride to form a second reaction mixture.

In another aspect, described herein is a process for preparing a compound, which is 2-(1-azabicyclo[2.2.2]oct-2-yl)-6-(3-methyl-1H-pyrazol-4-yl)thieno[3,2-d]pyrimidin-4(3H)-one, represented as Compound (VIII):

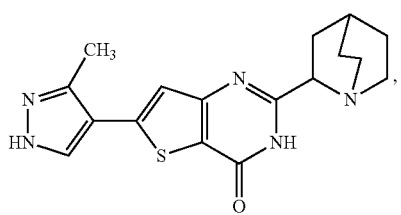

(VIII)

or a salt, hydrate, or tautomer thereof, or any combination thereof, wherein the process comprises:

deprotecting a compound represented as Compound (XXI):

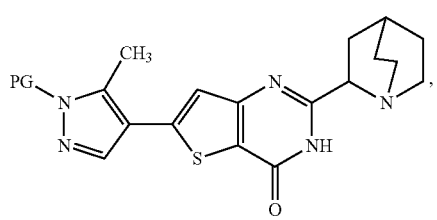

(XXI)

or a salt, hydrate, or tautomer thereof, or any combination thereof in a first reaction mixture, wherein PG is an amine protecting group;
treating the first reaction mixture with hydrogen chloride to form a second reaction mixture comprising a compound which is 2-(1-azabicyclo[2.2.2]oct-2-yl)-6-(3-methyl-1H-pyrazol-4-yl)thieno[3,2-d]pyrimidin-4(3H)-one dihydrochloride, represented as Compound (VII):

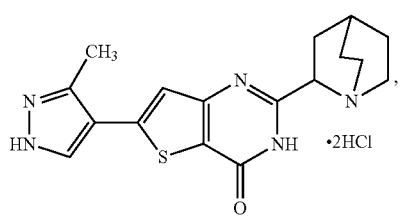

(VII)

or a hydrate or tautomer thereof, or any combination thereof; and
adding a base to the second reaction mixture to form a third reaction mixture.

In another aspect, described herein is a process for preparing a compound, which is methyl 3-amino-5-[1-(4-methoxybenzyl)-5-methyl-1H-pyrazol-4-yl]thiophene-2-carboxylate, represented as Compound (IV):

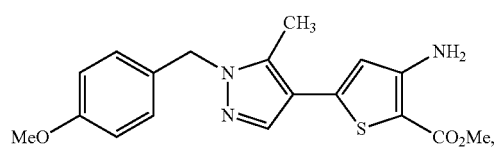

(IV)

or a salt, hydrate, or tautomer thereof, or any combination thereof, the process comprising: reacting 3-(1-(4-methoxybenzyl)-5-methyl-1H-pyrazol-4-yl)-3-oxopropanenitrile, represented as Compound (I):

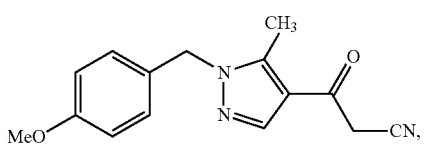

(I)

or a salt, hydrate, or tautomer thereof, or any combination thereof.

BRIEF DESCRIPTION OF THE DRAWINGS
FIG. 1 is a summary of the dynamic resolution study of Example 3 using (+)DBTA·H₂O.
DETAILED DESCRIPTION
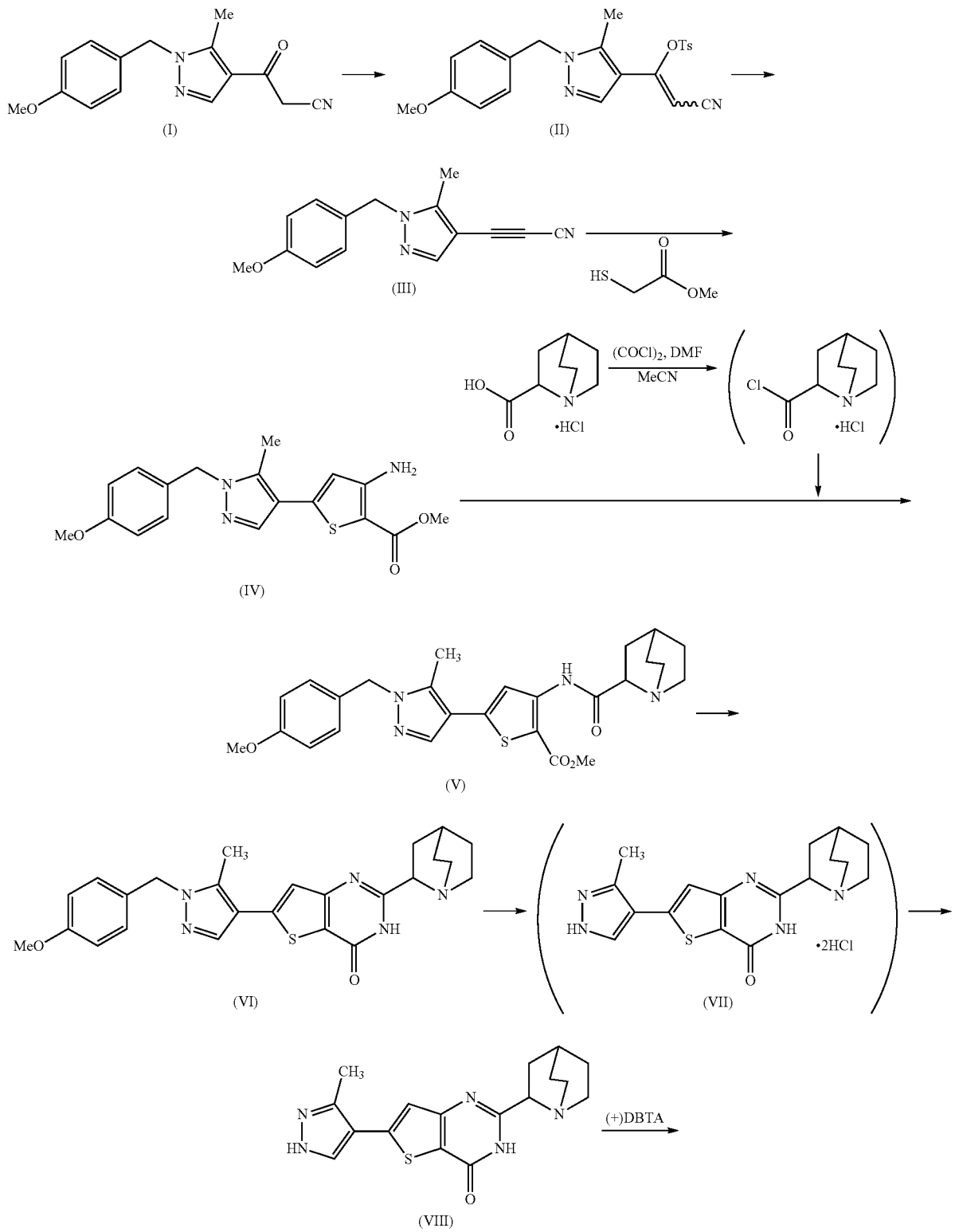

-continued

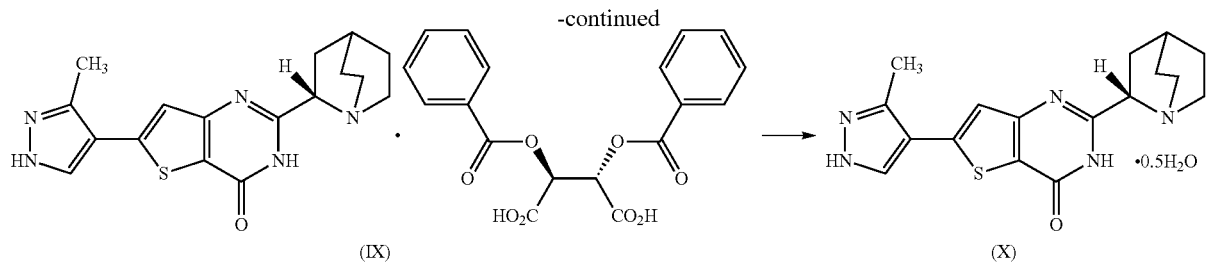

Scheme 2: Synthesis of Compound (I)

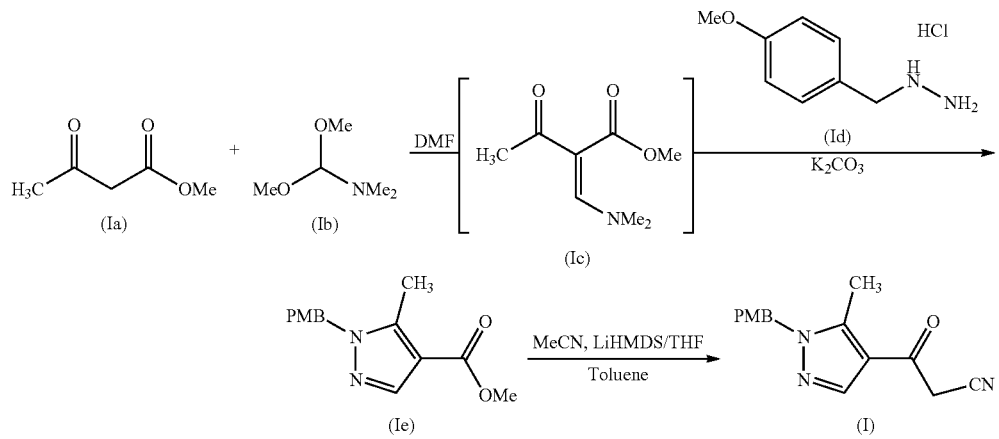

As used herein, when not modified by a prefix, such as hemi-, mono-, etc., the terms "hydrate" or "a hydrate" or "the hydrate" collectively refer to a solvate wherein the solvent molecule is $H_2O$ that is present in a defined stoichiometric amount, including, for example, hemihydrates, monohydrates, dihydrates, and trihydrates. The term "hemihydrate" refers to a hydrate with 1 mole of $H_2O$ per 2 moles of compound. The term "monohydrate" refers to a hydrate with 1 mole of $H_2O$ per mole of compound.

As used herein, the phrases "tautomer thereof" and the like are all understood to mean all tautomeric forms of compounds disclosed herein. As a non-limiting example, tautomerization of Compound XI may occur in the pyrazole and pyrimidinone groups of Compound XI. Specific non-limiting examples of tautomerization that may occur in Compound XI include:

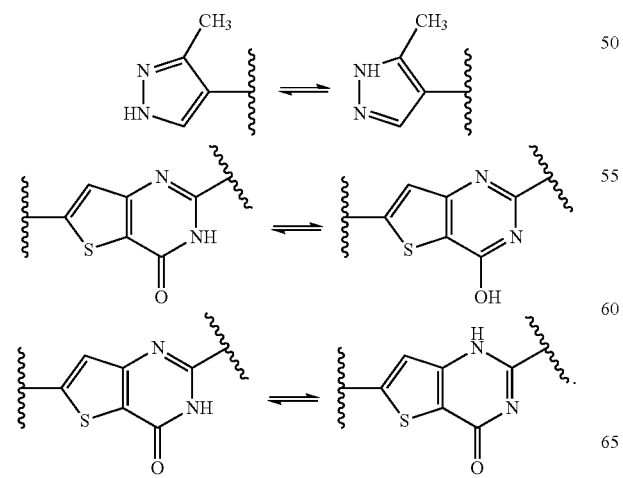

Specific non-limiting examples of isomeric structures of the tautomers included are:

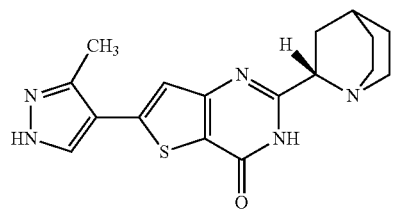 [SMILES: Cc1n[nH]cc1-c1cc2nc([C@@H]3CC4CCN3CC4)[nH]c(=O)c2s1]

2-[(2S)-1-azabicyclo[2.2.2]oct-2-yl]-6-(3-methyl-1H-pyrazol-4-yl)thieno[3,2-d]pyrimidin-4(3H)-one, and 2-[(2S)-1-azabicyclo[2.2.2]oct-2-yl]-6-(5-methyl-1H-pyrazol-4-yl)thieno[3,2-d]pyrimidin-4(3H)-one.

As used herein, the term "Dynamic Resolution" or "DR" refers to a type of chiral resolution where the (R) and (S) enantiomers can interconvert throughout the reaction process, such that a racemic compound can be converted into the desired enantiopure compound.

Examples of the "dynamic resolution promoter" or "DR promoter" in the present specification include reagent that may racemize a chiral center like tertiary amines, aliphatic carboxylic acids, and aromatic carboxylic acids. Tertiary amines in the present specification include triethylamine, 1,4-diazabicyclo[2.2.2]octane (DABCO), and 1,8-diazabicyclo[5.4.0]undec-7-ene (DBU). Aliphatic carboxylic acids in the present specification include formic acid, acetic acid, propionic acid and trifluoroacetic acid. Aromatic carboxylic acids in the present specification include benzoic acid. In one embodiment, the DR promoter is acetic acid.

Examples of chiral acids in the present specification include the compounds of formulas XIIa, XIIb, XIIIa, XIIIb, XIVa, and XIVb:

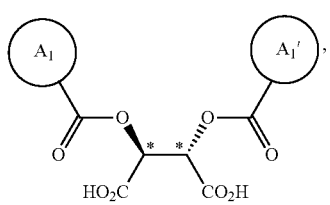
(XIIa)

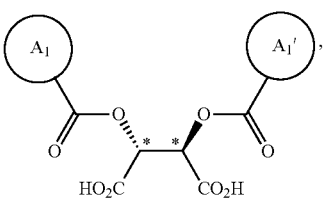
(XXIb)

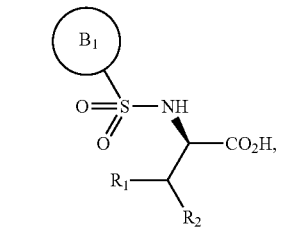
(XIIIa)

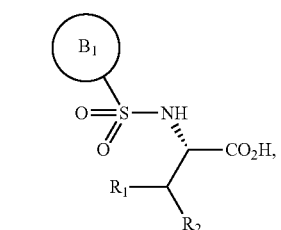
(XIIIb)

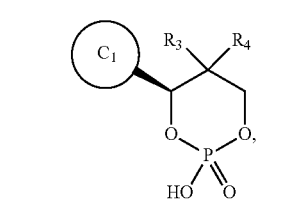
(XIVa)

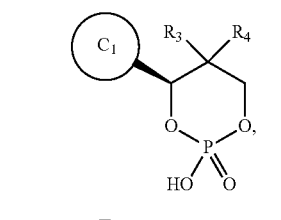
(XIVb)

or a hydrate thereof,
wherein ring $A_1$, ring $A_1'$, ring $B_1$ and ring $C_1$ are each independently i) aromatic hydrocarbon ring (for example, benzene ring), or ii) aromatic heterocyclic ring; and wherein $R_1$, $R_2$, $R_3$, and $R_4$ are each independently $C_{1-4}$alkyl. Ring $A_1$ is optionally substituted, for example, with 1, 2 or 3 substituents chosen from i) a $C_{1-4}$ alkyl group, ii) a $C_{1-4}$ alkoxy group or iii) a halogen atom and ring $A_1'$ is optionally substituted with 1, 2 or 3 substituents chosen from i) a $C_{1-4}$ alkyl group, ii) a $C_{1-4}$ alkoxy group or iii) a halogen atom; ring $B_1$ is optionally substituted, for example, with 1, 2 or 3 substituents chosen from i) a $C_{1-4}$ alkyl group, ii) a $C_{1-4}$ alkoxy group or iii) a halogen atom; $R_1$ is a $C_{1-4}$ alkyl group; and $R_2$ is a $C_{1-4}$ alkyl group;

the ring $C_1$ is optionally substituted, for example, with 1, 2 or 3 substituents chosen from i) a $C_{1-4}$ alkyl group, ii) a $C_{1-4}$ alkoxy group or iii) a halogen atom; $R_3$ is a $C_{1-4}$ alkyl group; and $R_4$ is a $C_{1-4}$ alkyl group.

Other examples of chiral acids in the present specification include the compounds of formula XIIc, XIId, XIIIc, XIIId, XIVc and XIVd:

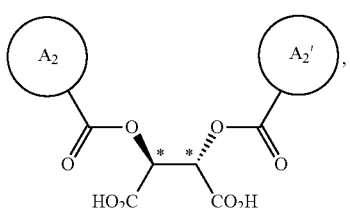
(XIIc)

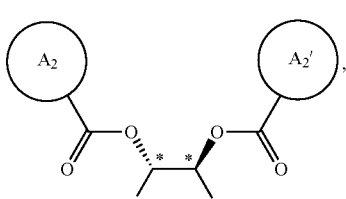
(XIId)

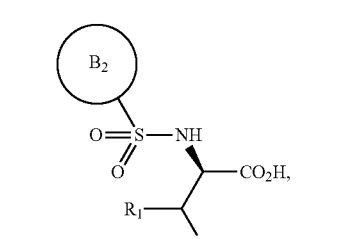
(XIIIc)

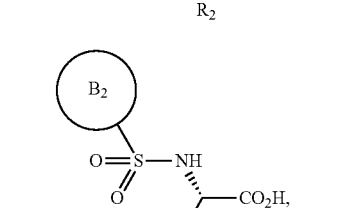
(XIIId)

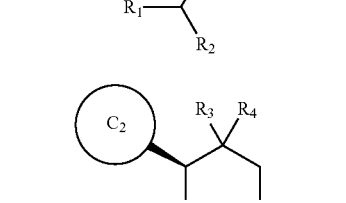
(XIVc)

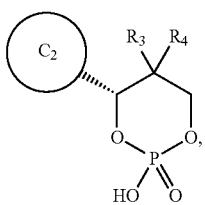
(XIVd)

or a hydrate thereof,
wherein ring $A_2$, ring $A_2'$, ring $B_2$ and ring $C_2$ are each independently i) 6-membered aromatic hydrocarbon ring (e.g. benzene ring), or ii) 5-membered or 6-membered nitrogen containing aromatic heterocyclic ring (for example, pyridine ring, pyrimidine ring);

ring $A_2$ is optionally substituted with 1, 2 or 3 substituents chosen from i) a $C_{1-4}$ alkyl group, ii) a $C_{1-4}$ alkoxy group or iii) a halogen atom and ring $A_2'$ is optionally substituted with 1, 2 or 3 substituents chosen from i) a $C_{1-4}$ alkyl group, ii) a $C_{1-4}$ alkoxy group or iii) a halogen atom;

the ring $B_2$ is optionally substituted with 1, 2 or 3 substituents chosen from i) a $C_{1-4}$ alkyl group, ii) a $C_{1-4}$ alkoxy group or iii) a halogen atom; $R_1$ is a $C_{1-4}$ alkyl group; and $R_2$ is a $C_{1-4}$ alkyl group; and the ring $C_2$ is optionally substituted with 1, 2 or 3 substituents chosen from i) a $C_{1-4}$ alkyl group, ii) a $C_{1-4}$ alkoxy group or iii) a halogen atom; $R_3$ is a $C_{1-4}$ alkyl group; and $R_4$ is a $C_{1-4}$ alkyl group.

Further examples of chiral acids in the present specification include the compounds of formulas XII, XIII and XIV:

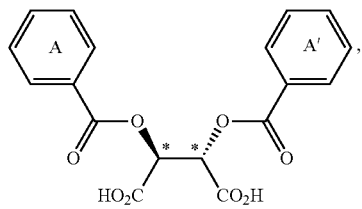
(XII)

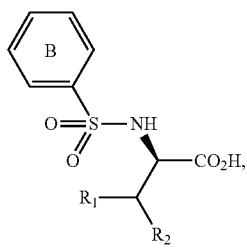
(XIII)

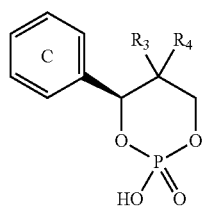
(XIV)

or a hydrate thereof,
wherein ring A is optionally substituted with 1, 2 or 3 substituents chosen from i) a $C_{1-4}$ alkyl group, ii) a $C_{1-4}$ alkoxy group or iii) a halogen atom and ring A' is optionally substituted with 1, 2 or 3 substituents chosen from i) a $C_{1-4}$ alkyl group, ii) a $C_{1-4}$ alkoxy group or iii) a halogen atom;

the ring B is optionally substituted with 1, 2 or 3 substituents chosen from i) a $C_{1-4}$ alkyl group, ii) a $C_{1-4}$ alkoxy group or iii) a halogen atom; $R_1$ is a $C_{1-4}$ alkyl group; and $R_2$ is a $C_{1-4}$ alkyl group, the ring C is optionally substituted with 1, 2 or 3 substituents chosen from i) a $C_{1-4}$ alkyl group, ii) a $C_{1-4}$ alkoxy group or iii) a halogen atom; $R_3$ is a $C_{1-4}$ alkyl group; and $R_4$ is a $C_{1-4}$ alkyl group. In one embodiment, the chiral acid is chosen from:

(XII)

(XV)

(XVI)

or a hydrate thereof,
wherein ring A is optionally substituted with 1, 2 or 3 substituents chosen from i) a $C_{1-4}$ alkyl group, ii) a $C_{1-4}$ alkoxy group or iii) a halogen atom and ring A' is optionally substituted with 1, 2 or 3 substituents chosen from i) a $C_{1-4}$ alkyl group, ii) a $C_{1-4}$ alkoxy group or iii) a halogen atom;

the ring B is optionally substituted with 1, 2 or 3 substituents chosen from i) a $C_{1-4}$ alkyl group, ii) a $C_{1-4}$ alkoxy group or iii) a halogen atom; and the ring C is optionally substituted with 1, 2 or 3 substituents chosen from i) a $C_{1-4}$ alkyl group, ii) a $C_{1-4}$ alkoxy group or iii) a halogen atom.

In another embodiment, the chiral acid may be chosen from:

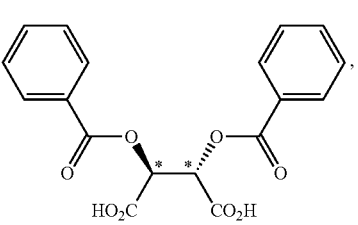
(XVII)

-continued (XVIII) 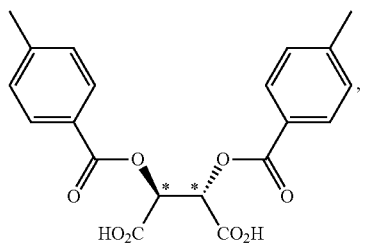

(XIX) 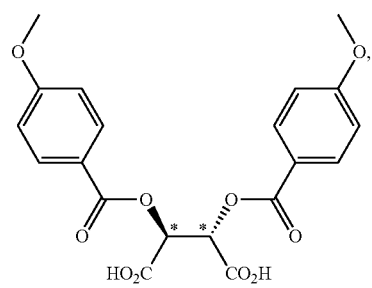

(XX) 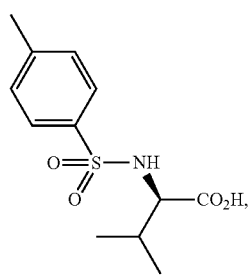

(XXIa) 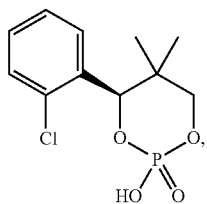

(XXII) 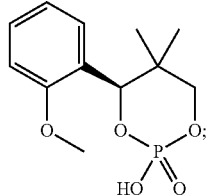

or a hydrate thereof.

In one embodiment, the chiral acid is (XVII) 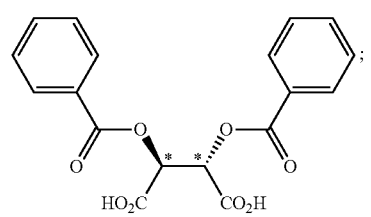

or a hydrate thereof.

Examples of the "$C_{1-4}$ alkyl group" in the present specification include methyl, ethyl, propyl, isopropyl, butyl, isobutyl, sec-butyl and tert-butyl. In one embodiment, the $C_{1-4}$ alkyl group is methyl.

Examples of the "$C_{1-4}$ alkoxy group" in the present specification include methoxy, ethoxy, propoxy, isopropoxy, butoxy, isobutoxy, sec-butoxy and tert-butoxy. In one embodiment, the $C_{1-4}$ alkoxy group is methoxy.

Unless otherwise specified, the "halogen atom" in the present specification means a fluorine atom, a chlorine atom, a bromine atom or an iodine atom. In one embodiment, the halogen atom is a chlorine atom.

Dynamic Resolution of this specification may be performed in the presence of a solvent. Examples of the "solvent" in the present specification include $C_{1-6}$ aliphatic alcohol. Examples of the "$C_{1-6}$ aliphatic alcohol" in the present specification include methanol, ethanol, 1-propanol, 2-propanol, 1-butanol, 2-butanol, 2-methyl-propan-1-ol, butan-2-ol, 2-methyl-propan-2-ol, 1-pentanol, 3-methyl-butan-1-ol, 1-hexanol, 2-methoxy-ethanol, 2-ethoxy-ethanol, 2-butoxy-ethanol, 2-(2-methoxy-ethoxy)-ethanol, 2-(2-ethoxy-ethoxy)-ethanol). In one embodiment, the solvent is 1-butanol. In another embodiment, the solvent is 2-butanol. In another embodiment, the solvent is toluene. In another embodiment, the solvent is water. In another embodiment, the solvent is heptane. In another embodiment, the solvent is acetonitrile. In another embodiment, the solvent is tetrahydrofuran. In another embodiment, the solvent is ethyl acetate.

Examples of the "base" in the present specification include an alkali metal base, an alkaline earth metal base, an organic amine base or an inorganic amine base. Examples of alkali metal bases and alkaline earth metal bases include, but are not limited to, potassium carbonate, sodium carbonate, calcium carbonate, lithium hydroxide, potassium hydroxide, sodium hydroxide, lithium hydrogen carbonate, potassium hydrogen carbonate, sodium hydrogen carbonate, lithium hydride, potassium hydride, sodium hydride, lithium tert-butoxide, potassium tert-butoxide, and sodium tert-butoxide.

Examples of other alkali metal bases include, but are not limited to, cesium carbonate, and cesium hydroxide.

Examples of organic amine bases include, but are not limited to, trialkylamines, cyclic amines, pyridines and substituted pyridines. Examples of these include, but are not limited to, triethylamine, triethylenediamine, pyridine, collidine, 2,6-lutidine, 4-dimethylaminopyridine, di-tert-butylpyridine, N-methylmorpholine, N-methylpiperidine, tetramethylguanidine, 1,8-diazabicyclo[5.4.0]undec-7-ene (DBU), 1,4-diazabicyclo[2.2.2]octane (DABCO), 1,5-diazabicycle[4.3.0]non-5-ene, and N,N-diisopropylethylamine.

Examples of other organic amine bases include, but are not limited to, 1-azabicyclo[2.2.2]octane, tributylamine, and tripropylamine. Examples of inorganic amine bases include, but are not limited to, ammonia.

Examples of the "polar solvent" in the present specification include, but are not limited to, acetonitrile, alcohols (e.g., methanol, ethanol, propanol, n-butanol etc.), ethers (e.g., tetrahydrofuran (THF), 1,4-dioxane, dimethoxyethane (DE) etc.) and amides (e.g., N,N-dimethylformamide (DMF), N,N-dimethylacetamide (DMAc), N-methylpyrrolidine (NMP) etc.). In one embodiment, the polar solvent is N,N-dimethylacetamide (DMAc).

As used herein, the term "amine protecting group" refers to a chemical group that: i) reacts with an amine functional group of a substrate to form a protected substrate; ii) is stable to reaction conditions to which the protected substrate will be subjected; and iii) is removable from a protected substrate to liberate the amine under conditions that are compatible with other functionality present in the substrate.

Amine protecting groups that are suitable for use in the processes and compounds of the present specification are known to those of ordinary skill in the art. The chemical properties of such protecting groups, methods for their introduction and their removal can be found, for example, in P. G. M. Wuts, *Greene's Protective Groups in Organic Synthesis* (5th ed.), John Wiley & Sons, NJ (2014), the disclosure of which is incorporated herein by reference.

Examples of the amine protecting group include formyl, $C_{1-6}$ alkyl-carbonyl (e.g., acetyl, propionyl), $C_{1-6}$ alkoxycarbonyl (e.g., methoxycarbonyl, ethoxycarbonyl, tert-butoxycarbonyl), benzoyl, $C_{7-10}$ aralkyl-carbonyl (e.g., benzylcarbonyl), $C_{7-14}$ aralkyloxy-carbonyl (e.g., benzyloxycarbonyl, 9-fluorenylmethoxycarbonyl), $C_{7-10}$ aralkyl (e.g., benzyl, p-methoxybenzyl), trityl, phthaloyl, N,N-dimethylaminomethylene, silyl (e.g., trimethylsilyl, triethylsilyl, dimethylphenylsilyl, tert-butyldimethylsilyl, tert-butyldiethylsilyl), $C_{2-6}$ alkenyl (e.g., 1-allyl) and the like. These groups are optionally substituted by 1 to 3 substituents selected from a halogen atom (e.g., a fluorine atom, a chlorine atom, a bromine atom, an iodine atom), $C_{1-6}$ alkoxy (e.g., methoxy, ethoxy, propoxy), nitro and the like.

In one embodiment, the amine protecting group is p-methoxybenzyl.

Examples of the "strong acid" in the present specification include a mineral acid, an organic acid and an acidic ion exchange resin. Examples of mineral acid include, but are not limited to, perchloric acid, hydrogen bromide, hydrogen chloride, sulfuric acid, nitric acid and phosphoric acid. Examples of organic acid include, but are not limited to, p-toluenesulfonic acid, benzenesulfonic acid, methanesulfonic acid, trifluoromethanesulfonic acid or trifluoroacetic acid. Examples of acidic ion exchange resin include, but are not limited to, Amberlyst® 15(H) or Dowex® 50WX2. In one embodiment, the strong acid is methanesulfonic acid.

Compounds and processes of this specification include those described generally above, and are further illustrated by the detailed descriptions of processes and compounds given below. Terms used herein shall be accorded the following defined meanings, unless otherwise indicated.

The term "substituted", as used herein, means that a hydrogen radical of the designated moiety is replaced with the radical of a specified substituent, provided that the substitution results in a stable or chemically feasible compound.

As used herein, the term "comprising" means "including, but not limited to".

As used herein, the symbol "*" in the formula of this specification means a chiral center. However, an atom which does not have this symbol may also be a chiral center.

Methods for determining diastereomeric and enantiomeric purity are well-known in the art. Diastereomeric purity can be determined by any analytical method capable of quantitatively distinguishing between a compound and its diastereomers. Examples of suitable analytical methods include, without limitation, nuclear magnetic resonance spectroscopy (NMR), gas chromatography (GC), and high performance liquid chromatography (HPLC). Similarly, enantiomeric purity can be determined by any analytical method capable of quantitatively distinguishing between a compound and its enantiomer. Examples of suitable analytical methods include, without limitation, GC or HPLC using a chiral column packing material. Enantiomers may also be distinguishable by GC or HPLC using an achiral column packing material if first derivatized with an optically enriched derivatizing agent, e.g., Mosher's acid. Similarly, enantiomers may also be distinguishable by NMR if first derivatized with an optically enriched derivatizing agent.

In one embodiment, the salt of compound XI is preferably a pharmacologically acceptable salt, and examples thereof include salts with inorganic bases, salts with organic bases, salts with inorganic acids, salts with organic acids, and salts with basic or acidic amino acids.

Examples of the salt with inorganic base include alkali metal salts such as a sodium salt, a potassium salt and the like; alkaline earth metal salts such as a calcium salt, a magnesium salt and the like; an aluminum salt and an ammonium salt. Examples of the salt with organic base include a salt with trimethylamine, triethylamine, pyridine, picoline, ethanolamine, diethanolamine, triethanolamine, tromethamine [tris(hydroxymethyl)methylamine], tert-butylamine, cyclohexylamine, benzylamine, dicyclohexylamine or N,N-dibenzylethylenediamine. Examples of the salt with inorganic acid include a salt with hydrogen chloride, hydrogen bromide, nitric acid, sulfuric acid or phosphoric acid. Examples of the salt with organic acid include a salt with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid or p-toluenesulfonic acid. Examples of the salt with organic acid also include a salt with the aforementioned compound (XII), (XIII), (XIV), (XV), (XVI), (XVII), (XVIII), (XIX), (XX), (XXIa), (XXII) or a hydrate thereof. Further, examples of the salt with organic acid also include a salt with the aforementioned compound (XIIa), (XIIb), (XIIc), (XIId), (XIIIa), (XIIIb), (XIIIc), (XIIId), (XIVa), (XIVb), (XIVc), (XIVd) or a salt thereof. Examples of the salt with basic amino acid include a salt with arginine, lysine or ornithine. Examples of the salt with acidic amino acid include a salt with aspartic acid or glutamic acid.

The processes and compounds of the present specification are further illustrated by the detailed description and illustrative examples given below. Specifically, the present invention provides the following [1] to [118].

[1] A process for preparing a compound, which is 2-[(2S)-1-azabicyclo[2.2.2]oct-2-yl]-6-(3-methyl-1H-pyrazol-4-yl)thieno[3,2-d]pyrimidin-4(3H)-one, represented as Compound (XI):

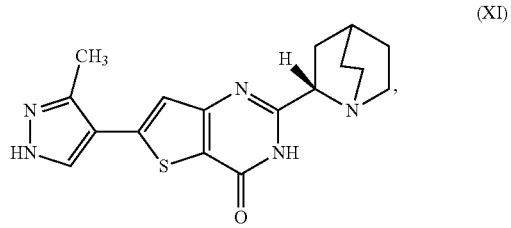 [SMILES: Cc1n[nH]cc1-c1cc2nc([C@@H]3CC4CCN3CC4)[nH]c(=O)c2s1]

or a salt, hydrate, or tautomer thereof, or any combination thereof, the process comprising converting a chiral center of 2-(1-azabicyclo[2.2.2]oct-2-yl)-6-(3-methyl-1H-pyrazol-4-yl)thieno[3,2-d]pyrimidin-4(3H)-one, represented as Compound (VIII):

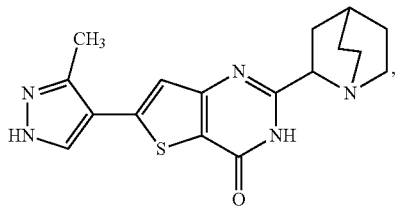

(VIII)

or a salt, hydrate, or tautomer thereof, or any combination thereof, to form the Compound (XI) or salt, hydrate, or tautomer thereof, or combination thereof.

[1'] The process according to [1], wherein the 2-[(2S)-1-azabicyclo[2.2.2]oct-2-yl]-6-(3-methyl-1H-pyrazol-4-yl)thieno[3,2-d]pyrimidin-4(3H)-one, as Compound (XI):

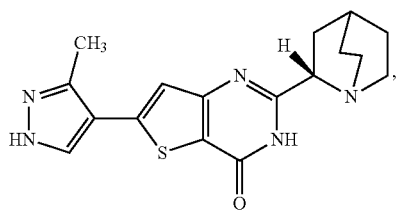

(XI)

or salt, hydrate, or tautomer thereof, or combination thereof is 2-[(2S)-1-azabicyclo[2.2.2]oct-2-yl]-6-(3-methyl-1H-pyrazol-4-yl)thieno[3,2-d]pyrimidin-4(3H)-one hemihydrate or a tautomer thereof, or combination thereof.

[2] The process according to [1], wherein the converting of the chiral center of 2-(1-azabicyclo[2.2.2]oct-2-yl)-6-(3-methyl-1H-pyrazol-4-yl)thieno[3,2-d]pyrimidin-4(3H)-one as the Compound (VIII), or salt, hydrate, or tautomer thereof, or combination thereof comprises:

heating a first reaction mixture comprising 2-(1-azabicyclo[2.2.2]oct-2-yl)-6-(3-methyl-1H-pyrazol-4-yl)thieno[3,2-d]pyrimidin-4(3H)-one as the Compound (VIII), or salt, hydrate, or tautomer thereof, or combination thereof, with a composition comprising a dynamic resolution promoter and a solvent to a temperature in a range between about 50° C. and about 90° C. (e.g., between about 80 and about 90° C.);

to the first reaction mixture, adding (2S,3S)-2,3-bis(benzoyloxy)butanedioic acid monohydrate in a solvent to form a (+) DBTA solution;

adding an additional solvent to the (+)DBTA solution at a temperature in a range between about 50° C. and about 90° C. (e.g., between about 80 and about 90° C.) to produce a second reaction mixture;

stirring the second reaction mixture at a temperature in a range between about 50° C. and about 90° C. (e.g., between about 80 and about 90° C.) for at least 3 hours;

adding ethyl acetate to the second reaction mixture while maintaining the temperature of the second reaction mixture in the range between about 50° C. and about 90° C. (e.g., between about 80 and about 90° C.) to form a third reaction mixture;

stirring the third reaction mixture at a temperature in a range between about 50° C. and about 90° C. (e.g., between about 80 and about 90° C.) for at least 1 hour;

cooling the third reaction mixture to a temperature in a range between about 20° C. and about 30° C., while stirring the third reaction mixture for at least about 1 hour;

collecting resulting solids in the third reaction mixture by filtration;

washing the solids at least with ethyl acetate;

drying the washed solids to give (2S,3S)-2,3-bis(benzoyloxy)butanedioic acid 2-1(2S)-1-azabicyclo[2.2.2]oct-2-yl-6-(3-methyl-1H-pyrazol-4-yl)thieno[3,2-d]pyrimidin-4(3H)-one(1:1);

dissolving the (2S,3S)-2,3-bis(benzoyloxy)butanedioic acid 2-[(2S)-1-azabicyclo[2.2.2]oct-2-yl]-6-(3-methyl-1H-pyrazol-4-yl)thieno[3,2-d]pyrimidin-4(3H)-one(1:1) in a mixture of acetone and water at a temperature in a range between about 0° C. and about 10° C.;

adding aqueous ammonium hydroxide solution to a first resulting solution in which the (2S,3S)-2,3-bis(benzoyloxy)butanedioic acid 2-[(2S)-1-azabicyclo[2.2.2]oct-2-yl]-6-(3-methyl-1H-pyrazol-4-yl)thieno[3,2-d]pyrimidin-4(3H)-one (1:1) is dissolved, to form a second resulting solution;

stirring the second resulting solution and maintaining the temperature in a range between about 0° C. and about 10° C. for at least 1 hour;

adding acetone to the stirred second resulting solution and maintaining the temperature in a range between about 0° C. and about 10° C.;

stirring the second resulting solution comprising acetone at a temperature in a range between about 20° C. and about 30° C. for at least 1 hour;

collecting second solids from the stirred second resulting solution by filtration;

washing the second solids with water; and washing the water-washed second solids with acetone to give 2-[(2S)-1-azabicyclo[2.2.2]oct-2-yl]-6-(3-methyl-1H-pyrazol-4-yl)thieno[3,2-d]pyrimidin-4(3H)-one hemihydrate or a tautomer thereof or any combination thereof.

[3] The process according to [1], wherein the converting of the chiral center of 2-(1-azabicyclo[2.2.2]oct-2-yl)-6-(3-methyl-1H-pyrazol-4-yl)thieno[3,2-d]pyrimidin-4(3H)-one as the Compound (VIII) or salt, hydrate, or tautomer thereof, or combination thereof comprises:

heating a first reaction mixture comprising 2-(1-azabicyclo[2.2.2]oct-2-yl)-6-(3-methyl-1H-pyrazol-4-yl)thieno[3,2-d]pyrimidin-4(3H)-one as the Compound (VIII), or salt, hydrate, or tautomer thereof, or combination thereof, with a composition comprising a dynamic resolution promoter, a first solvent, and (2S,3S)-2,3-bis(benzoyloxy)butanedioic acid monohydrate to a temperature of about 80° C.;

adding (2S,3S)-2,3-bis(benzoyloxy)butanedioic acid monohydrate in a second solvent at a temperature in a range between about 85° C. and about 90° C. to the first reaction mixture, to form a second reaction mixture, stirring the second reaction mixture at a temperature of about 90° C. for about 8 hours;

cooling the stirred second reaction mixture to room temperature, while stirring for at least 1 hour;

collecting solids from the stirred second reaction mixture by filtration;

washing the solids at least with ethyl acetate;

drying the washed solids to give 2-((2S)-1-azabicyclo[2.2.2]oct-2-yl)-6-(3-methyl-lli-pyrazol-4-yl)thieno[3,2-d]pyrimidin-4(3H)-one·(2S,3S)-2,3-bis(benzoyloxy)butanedioic acid;

dissolving the 2-((2S)-1-azabicyclo[2.2.2]oct-2-yl)-6-(3-methyl-1H-pyrazol-4-yl)thieno[3,2-d]pyrimidin-4(3H)-one·(2S,3S)-2,3-bis(benzoyloxy)butanedioic acid in di-methyl sulfoxide;

adding an aqueous solution comprising ammonium hydroxide to the resulting di-methyl sulfoxide solution to form a third reaction mixture;

heating the third reaction mixture to a temperature of about 50° C.;
adding a mixture comprising water and acetone to the heated third reaction mixture at a temperature of about 50° C. to form a fourth reaction mixture;
cooling the fourth reaction mixture to room temperature while stirring for about 2 hours;
collecting second solids from the cooled fourth reaction mixture by filtration;
washing the second solids at least with water and acetone; and
washing the washed second solids with acetone to give 2-[(2S)-1-azabicyclo[2.2.2]oct-2-yl]-6-(3-methyl-1H-pyrazol-4-yl)thieno[3,2-d]pyrimidin-4(3H)-one hemihydrate, a tautomer thereof, or any combination thereof.

[4] The process according to [1], wherein the converting of the chiral center of 2-(1-azabicyclo[2.2.2]oct-2-yl)-6-(3-methyl-1H-pyrazol-4-yl)thieno[3,2-d]pyrimidin-4(3H)-one as the Compound (VIII), or a salt, hydrate or tautomer thereof, or combination thereof comprises treating 2-(1-azabicyclo[2.2.2]oct-2-yl)-6-(3-methyl-1H-pyrazol-4-yl)thieno[3,2-d]pyrimidin-4(3H)-one as the Compound (VIII), or a salt, hydrate or tautomer thereof, or combination thereof, with a chiral acid in the presence of a dynamic resolution promoter to produce a chiral acid salt of the 2-[(2S)-1-azabicyclo[2.2.2]oct-2-yl]-6-(3-methyl-1H-pyrazol-4-yl)thieno[3,2-d]pyrimidin-4(3H)-one.

[5] The process according to [4], wherein the converting of the chiral center of the 2-(1-azabicyclo[2.2.2]oct-2-yl)-6-(3-methyl-1H-pyrazol-4-yl)thieno[3,2-d]pyrimidin-4(3H)-one as the Compound (VIII), or salt, hydrate, or tautomer thereof, or combination thereof, comprises treating the 2-(1-azabicyclo[2.2.2]oct-2-yl)-6-(3-methyl-1H-pyrazol-4-yl)thieno[3,2-d]pyrimidin-4(3H)-one as the Compound (VIII), or salt, hydrate, or tautomer thereof, or combination thereof in a dynamic resolution promoter with a chiral acid to produce the chiral acid salt of 2-[(2S)-1-azabicyclo[2.2.2]oct-2-yl]-6-(3-methyl-1H-pyrazol-4-yl)thieno[3,2-d]pyrimidin-4(3H)-one.

[6] The process according to [4], wherein the chiral acid is at least one acid selected from the group consisting of:

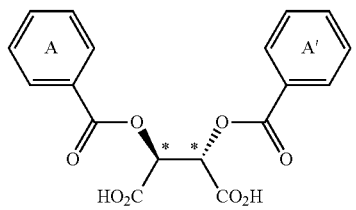

(XII)

or a hydrate thereof, wherein ring A is optionally substituted with 1, 2, or 3 substituents selected from the group consisting of a $C_{1-4}$ alkyl group, a $C_{1-4}$ alkoxy group, and a halogen atom, and ring A' is optionally substituted with 1, 2, or 3 substituents selected from the group consisting of a $C_{1-4}$ alkyl group, a $C_{1-4}$ alkoxy group, and a halogen atom;

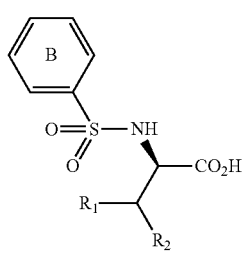

(XIII)

or a hydrate thereof, wherein ring B is optionally substituted with 1, 2, or 3 substituents selected from the group consisting of a $C_{1-4}$ alkyl group, a $C_{1-4}$ alkoxy group, and a halogen atom; $R_1$ is a $C_{1-4}$ alkyl group, and $R_2$ is a $C_{1-4}$ alkyl group; and

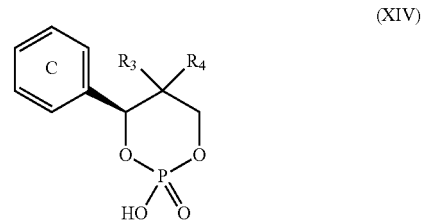

(XIV)

or a hydrate thereof, wherein ring C is optionally substituted with 1, 2, or 3 substituents selected from the group consisting of a $C_{1-4}$ alkyl group, a $C_{1-4}$ alkoxy group, and a halogen atom, $R_3$ is a $C_{1-4}$ alkyl group, and $R_4$ is a $C_{1-4}$ alkyl group.

[6'] The process according to [4], wherein the chiral acid is at least one acid selected from the group consisting of:

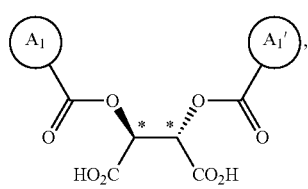

(XIIa)

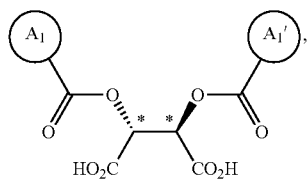

(XIIb)

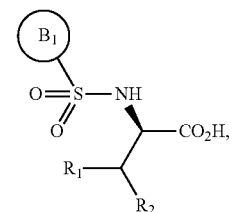

(XIIIa)

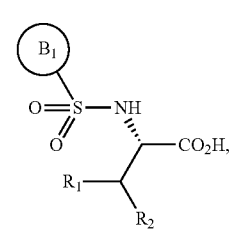

(XIIIb)

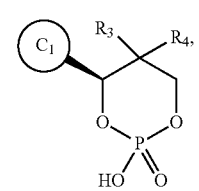

(XIVa)

(XIVb)

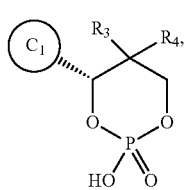

(XIVd)

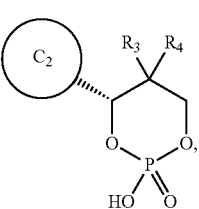

or a hydrate thereof, wherein ring $A_1$, ring $A_1'$, ring $B_1$ and ring $C_1$ are each independently i) aromatic hydrocarbon ring (for example, benzene ring) which is optionally substituted, or ii) aromatic heterocyclic ring which is optionally substituted; and wherein $R_1$, $R_2$, $R_3$, and $R_4$ are each independently $C_{1-4}$ alkyl.

[6"] The process according to [4], wherein the chiral acid is at least one acid selected from the group consisting of:

(XIIc)

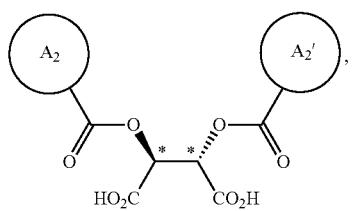

(XIId)

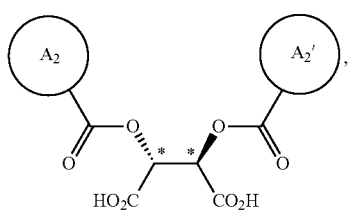

(XIIIc)

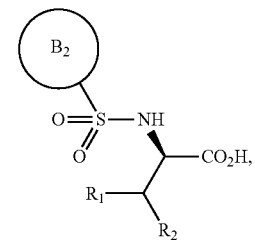

(XIIId)

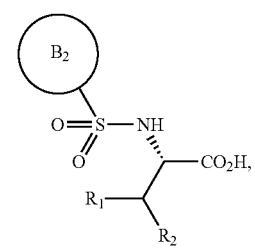

(XIVc)

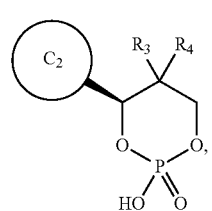

or a hydrate thereof, wherein ring $A_2$, ring $A_2'$, ring $B_2$ and ring $C_2$ are each independently i) 6-membered aromatic hydrocarbon ring (e.g. benzene ring), or ii) 5-membered or 6-membered nitrogen containing aromatic heterocyclic ring (for example, pyridine ring, pyrimidine ring);

ring $A_2$ is optionally substituted with 1, 2 or 3 substituents chosen from i) a $C_{1-4}$ alkyl group, ii) a $C_{1-4}$ alkoxy group or iii) a halogen atom and ring $A_2^1$ is optionally substituted with 1, 2 or 3 substituents chosen from i) a $C_{1-4}$ alkyl group, ii) a $C_{1-4}$ alkoxy group or iii) a halogen atom;

the ring $B_2$ is optionally substituted with 1, 2 or 3 substituents chosen from i) a $C_{1-4}$ alkyl group, ii) a $C_{1-4}$ alkoxy group or iii) a halogen atom; $R_1$ is a $C_{1-4}$ alkyl group; and $R_2$ is a $C_{1-4}$ alkyl group; and the ring $C_2$ is optionally substituted with 1, 2 or 3 substituents chosen from i) a $C_{1-4}$ alkyl group, ii) a $C_{1-4}$ alkoxy group or iii) a halogen atom; $R_3$ is a $C_{1-4}$ alkyl group; and $R_4$ is a $C_{1-4}$ alkyl group.

[7] The process according to [4], wherein the chiral acid is at least one acid selected from the group consisting of:

(XII)

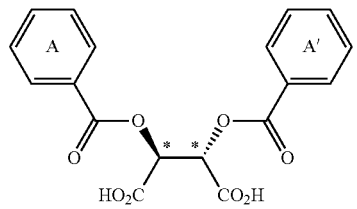

or a hydrate thereof, wherein ring A is optionally substituted with 1, 2, or 3 substituents selected from the group consisting of a $C_{1-4}$ alkyl group, a $C_{1-4}$ alkoxy group, and a halogen atom, and ring A' is optionally substituted with 1, 2, or 3 substituents selected from the group consisting of a $C_{1-4}$ alkyl group, a $C_{1-4}$ alkoxy group, and a halogen atom;

(XV)

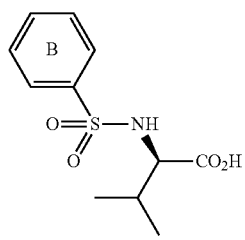

or a hydrate thereof, wherein ring B is optionally substituted with 1, 2, or 3 substituents selected from the group consisting of a $C_{1-4}$ alkyl group, a $C_{1-4}$ alkoxy group, and a halogen atom; and

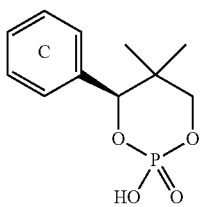
(XVI)

or a hydrate thereof, wherein ring C is optionally substituted with 1, 2, or 3 substituents selected from the group consisting of a $C_{1-4}$ alkyl group, a $C_{1-4}$ alkoxy group, and a halogen atom.

[8] The process according to [4], wherein the chiral acid is at least one acid selected from the group consisting of:

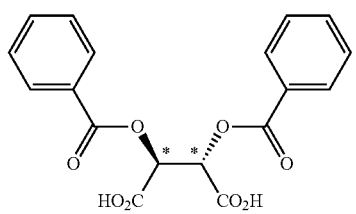
(XVII)

or a hydrate thereof;

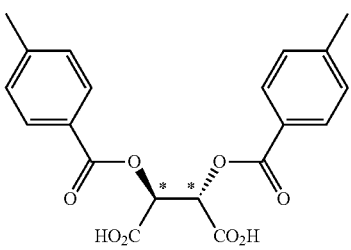
(XVIII)

or a hydrate thereof;

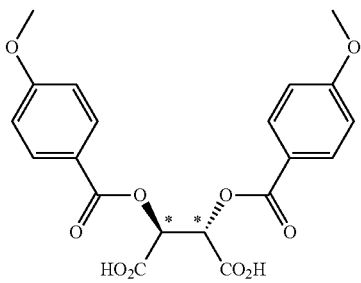
(XIX)

or a hydrate thereof;

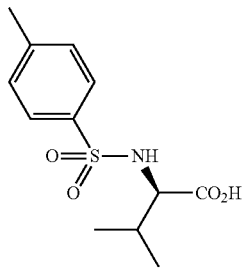
(XX)

or a hydrate thereof;

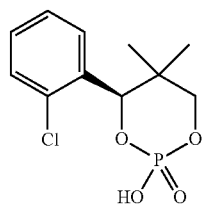
(XXI)

or a hydrate thereof; and

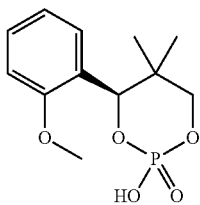
(XXII)

or a hydrate thereof.

[9] The process according to [4], wherein the dynamic resolution promoter comprises formic acid, acetic acid, propionic acid, trifluoroacetic acid, benzoic acid, triethylamine, 1,4-diazabicyclo[2.2.2]octane, or diazabicycloundecene.

[10] The process according to [4], wherein the dynamic resolution promoter comprises acetic acid.

[11] The process according to [4], wherein the treating of the 2-(1-azabicyclo[2.2.2]oct-2-yl)-6-(3-methyl-1H-pyrazol-4-yl)thieno[3,2-d]pyrimidin-4(3H)-one as the Compound (VIII), or salt, hydrate, or tautomer thereof, or combination thereof with the chiral acid in the presence of the dynamic resolution promoter is performed in the presence of a solvent.

[12] The process according to [11], wherein the solvent comprises at least one material selected from the group consisting of water, toluene, heptane, tetrahydrofuran, $C_{1-6}$ aliphatic alcohol, and ethyl acetate.

[13] The process according to [11], wherein the solvent comprises 1-butanol.

[14] The process according to [11], wherein the solvent comprises 2-butanol.

[15] The process according to [1], further comprising converting a chiral acid salt of 2-[(2S)-1-azabicyclo[2.2.2]oct-2-yl]-6-(3-methyl-1H-pyrazol-4-yl)thieno[3,2-d]pyrimidin-4(3H)-one to 2-[(2S)-1-azabicyclo[2.2.2]oct-2-yl]-6-(3-methyl-1H-pyrazol-4-yl)thieno[3,2-d]pyrimidin-4(3H)-one, or a hydrate or tautomer thereof, or any combination thereof.

[15'] The process according to [15], further comprising converting a chiral acid salt of 2-[(2S)-1-azabicyclo[2.2.2]oct-2-yl]-6-(3-methyl-1H-pyrazol-4-yl)thieno[3,2-d]pyrimidin-4(3H)-one to 2-[(2S)-1-azabicyclo[2.2.2]oct-2-yl]-6-(3-methyl-1H-pyrazol-4-yl)thieno[3,2-d]pyrimidin-4(3H)-one hemihydrate or a tautomer thereof, or any combination thereof.

[16] A process for preparing a chiral acid salt of 2-[(2S)-1-azabicyclo[2.2.2]oct-2-yl]-6-(3-methyl-1H-pyrazol-4-yl)thieno[3,2-d]pyrimidin-4(3H)-one, represented as Compound (XI):

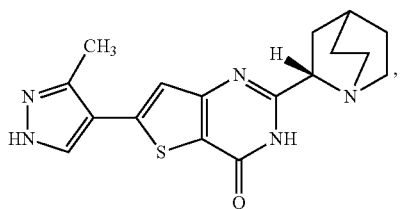

or a hydrate or tautomer thereof, or any combination thereof, wherein the process comprises reacting 2-(1-azabicyclo[2.2.2]oct-2-yl)-6-(3-methyl-1H-pyrazol-4-yl)thieno[3,2-d]pyrimidin-4(3H)-one, represented as Compound (VIII):

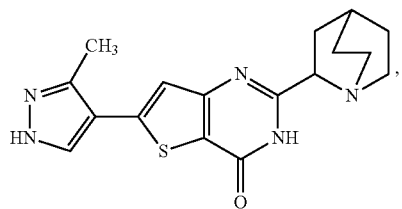

or a hydrate or tautomer thereof, or any combination thereof, with a chiral acid in a dynamic resolution promoter to produce the chiral acid salt of 2-[(2S)-1-azabicyclo[2.2.2]oct-2-yl]-6-(3-methyl-1H-pyrazol-4-yl)thieno[3,2-d]pyrimidin-4(3H)-one (Compound (XI)), or hydrate or tautomer thereof, or combination thereof.

[17] The process according to [16], wherein the process further comprises heating a first reaction mixture comprising 2-(1-azabicyclo[2.2.2]oct-2-yl)-6-(3-methyl-1H-pyrazol-4-yl)thieno[3,2-d]pyrimidin-4(3H)-one as the Compound (VIII), or hydrate or tautomer thereof, or combination thereof, with the dynamic resolution promoter and a first solvent to a temperature in a range between about 75° C. and about 95° C.

[18] The process according to [17], wherein the first reaction mixture is heated to a temperature in a range between about 80° C. and about 90° C.

[19] The process according to [17], further comprising adding the chiral acid dissolved in a second solvent to the first reaction mixture to form a second reaction mixture.

[20] The process according to [19], wherein the second reaction mixture is stirred at a temperature in a range between about 75° C. and about 95° C. for at least 3 hours.

[21] The process according to [20], wherein the second reaction mixture is stirred at a temperature in a range from about 80° C. to about 90° C.

[22] The process according to [20], wherein the second reaction mixture is stirred for a period selected from the group consisting of a period from about 3 hours to about 6 hours, a period from about 3 hours to about 12 hours, and a period from about 3 to about 24 hours.

[23] The process according to [19], wherein the process further comprises adding an additional solvent to the second reaction mixture, wherein the additional solvent and the second reaction mixture have the same temperature.

[24] The process according to [23], further comprising adding ethyl acetate to the second reaction mixture while maintaining a temperature of the second reaction mixture in a range between about 30° C. and about 95° C.

[25] The process according to [24], wherein the temperature is in a range selected from the group consisting of a range between about 30° C. and about 90° C., a range between about 60° C. and about 90° C., and a range between about 80° C. and about 90° C.

[26] The process according to [19], wherein the second reaction mixture is stirred at a temperature of about 90° C. for about 8 hours.

[26'] The process according to [19], wherein the second reaction mixture is stirred at a temperature of about 84° C. for about 27 hours.

[26''] The process according to [19], wherein the second reaction mixture is stirred at a temperature selected from the group consisting of a range between about 75° C. and about 92° C., a range between about 82° C. and about 92° C., a range between about 82° C. and about 86° C., and a temperature of about 84° C.

[27] The process according to [19], further comprising cooling the second reaction mixture to room temperature.

[28] The process according to [27], wherein the cooled second reaction mixture is stirred at room temperature for at least 1 hour.

[29] The process according to [28], wherein the cooled second reaction mixture is stirred at room temperature for a period selected from the group consisting of about 1 hour, about 3 hours, and about 5 hours.

[30] The process according to [27] further comprising collecting solids by filtration.

[31] The process according to [30], further comprising washing the solids at least with ethyl acetate.

[32] A process for preparing 2-[(2S)-1-azabicyclo[2.2.2]oct-2-yl]-6-(3-methyl-1H-pyrazol-4-yl)thieno[3,2-d]pyrimidin-4(3H)-one, represented as Compound (XI):

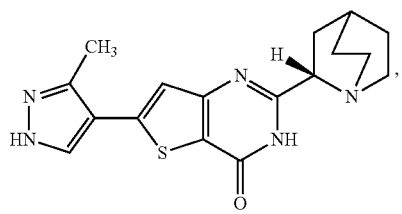

or a salt, hydrate, or tautomer thereof, or any combination thereof, the process comprising treating a chiral acid salt of 2-[(2S)-1-azabicyclo[2.2.2]oct-2-yl]-6-(3-methyl-1H-pyrazol-4-yl)thieno[3,2-d]pyrimidin-4(3H)-one with a base.

[32'] The process according to [32], wherein the 2-[(2S)-1-azabicyclo[2.2.2]oct-2-yl]-6-(3-methyl-1H-pyrazol-4-yl)thieno[3,2-d]pyrimidin-4(3H)-one, as Compound (XI):

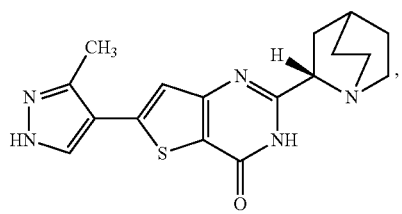

or salt, hydrate, or tautomer thereof, or combination thereof is 2-[(2S)-1-azabicyclo[2.2.2]oct-2-yl]-6-(3-methyl-1H-pyrazol-4-yl)thieno[3,2-d]pyrimidin-4(3H)-one hemihydrate or a tautomer thereof, or any combination thereof.

[33] The process according to [32] or [32'], wherein the base comprises aqueous ammonium hydroxide, and wherein the treating of the chiral acid salt with the base comprises adding the base to the chiral acid salt of 2-[(2S)-1-azabicyclo[2.2.2]oct-2-yl]-6-(3-methyl-1H-pyrazol-4-yl)thieno[3,2-d]pyrimidin-4(3H)-one as the Compound (XI), dissolved in dimethyl sulfoxide and water at a temperature in a range of about 35° C. or lower until a reaction mixture of the base and the chiral acid salt dissolved in dimethyl sulfoxide and water has a pH in a range between 8.5 and 9.0.

[34] The process according to [33], wherein the temperature is selected from the group consisting of about 25° C., about 30° C., and about 35° C.

[35] The process according to [33], further comprising heating the reaction mixture to about 50° C.

[36] The process according to [35], further comprising adding acetone and water to the reaction mixture at about 50° C.

[37] A process for preparing a compound, which is 2-(1-azabicyclo[2.2.2]oct-2-yl)-6-[1-(4-methoxybenzyl)-5-methyl-1H-pyrazol-4-yl]thieno[3,2-d]pyrimidin-4(3H)-one, represented as Compound (VI):

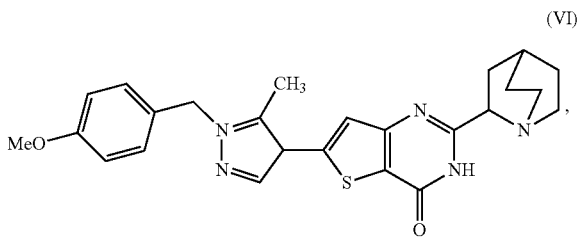

(VI)

or a salt, hydrate, or tautomer thereof, or any combination thereof, the process comprising: treating a compound, which is methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate, represented as Compound (V):

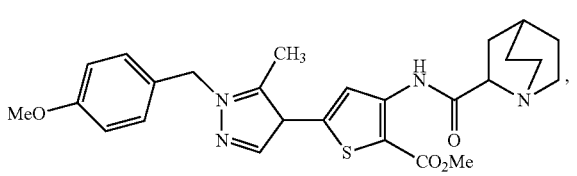

(V)

or a salt, hydrate, or tautomer thereof, or any combination thereof, with a mixture comprising formamide and a base to form the Compound (VI) or salt, hydrate, or tautomer thereof, or combination thereof.

[38] The process according to [37], wherein the base comprises potassium tert-butoxide.

[39] The process according to [37], wherein the mixture further comprises a polar solvent.

[40] The process according to [39], wherein the polar solvent comprises N,N-dimethylacetamide.

[41] The process according to [37], further comprising heating a reaction mixture comprising methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate, as the Compound (V), or salt, hydrate, or tautomer thereof, or combination thereof, with formamide and a base to a temperature in a range between about 25° C. and about 70° C. for at least 1 hour.

[42] The process according to [41], wherein the reaction mixture is heated for a period selected from the group consisting of about 1 hour, about 8 hours, about 16 hours, and about 24 hours.

[43] The process according to [41], wherein the reaction mixture is heated to a temperature selected from the group consisting of a range between about 25° C. and about 70° C., a range between about 45° C. and about 70° C., and a temperature of about 70° C.

[44] The process according to [37], further comprising preparing 2-[(2S)-1-azabicyclo[2.2.2]oct-2-yl]-6-(3-methyl-1H-pyrazol-4-yl)thieno[3,2-d]pyrimidin-4(3H)-one, represented as Compound (XI):

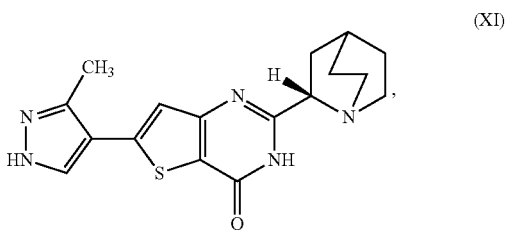 [SMILES: Cc1n[nH]cc1-c1cc2nc([C@@H]3CC4CCN3CC4)[nH]c(=O)c2s1]

(XI)

or a salt, hydrate, or tautomer thereof, or any combination thereof from the Compound (VI) or salt, hydrate, or tautomer thereof, or combination thereof.

[44'] The process according to [44], wherein the 2-[(2S)-1-azabicyclo[2.2.2]oct-2-yl]-6-(3-methyl-1H-pyrazol-4-yl)thieno[3,2-d]pyrimidin-4(3H)-one, as Compound (XI):

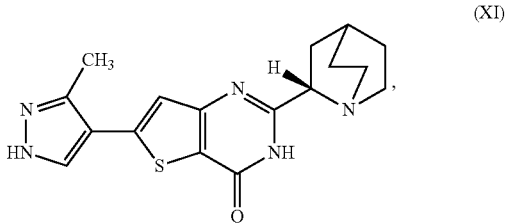 [SMILES: Cc1n[nH]cc1-c1cc2nc([C@@H]3CC4CCN3CC4)[nH]c(=O)c2s1]

(XI)

or salt, hydrate, or tautomer thereof, or combination thereof is 2-[(2S)-1-azabicyclo[2.2.2]oct-2-yl]-6-(3-methyl-1H-pyrazol-4-yl)thieno[3,2-d]pyrimidin-4(3H)-one hemihydrate or a tautomer thereof, or any combination thereof.

[44"] A process for preparing a compound, which is 2-[(2S)-1-azabicyclo[2.2.2]oct-2-yl]-6-(3-methyl-1H-pyrazol-4-yl)thieno[3,2-d]pyrimidin-4(3H)-one, represented as Compound (XI):

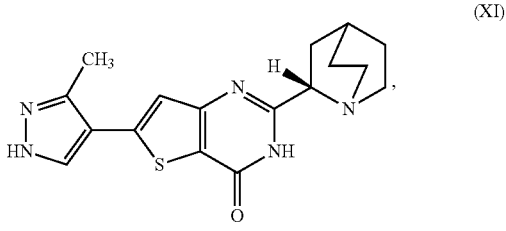 [SMILES: Cc1n[nH]cc1-c1cc2nc([C@@H]3CC4CCN3CC4)[nH]c(=O)c2s1]

(XI)

or a salt, hydrate, or tautomer thereof, or any combination thereof, the process comprising:

(i) preparing a compound, which is 2-(1-azabicyclo[2.2.2]oct-2-yl)-6-[1-(4-methoxybenzyl)-5-methyl-1H-pyrazol-4-yl]thieno[3,2-d]pyrimidin-4(3H)-one, represented as Compound (VI):

(VI)

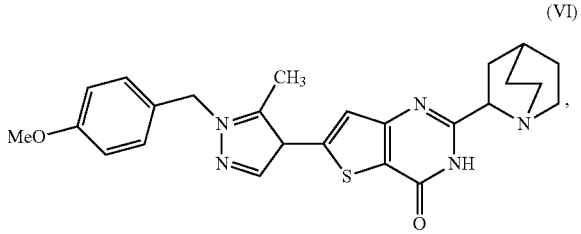

or a salt, hydrate, or tautomer thereof, or any combination thereof
by treating a compound, which is methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate, represented as Compound (V):

(V)

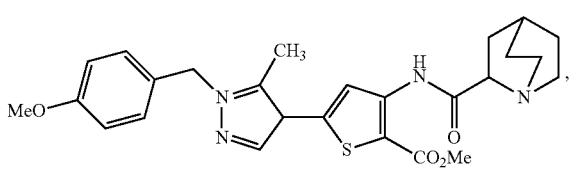

or a salt, hydrate, or tautomer thereof, or any combination thereof, with a mixture comprising formamide and a base to form the Compound (VI) or salt, hydrate, or tautomer thereof, or combination thereof;

(ii) preparing a compound, which is 2-(1-azabicyclo[2.2.2]oct-2-yl)-6-(3-methyl-1H-pyrazol-4-yl)thieno[3,2-d]pyrimidin-4(3H)-one, represented as Compound (VIII):

(VIII)

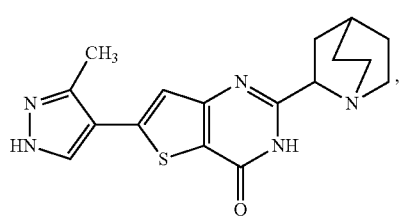

or a salt, hydrate, or tautomer thereof, or any combination thereof
by deprotecting Compound (VI) or a salt, hydrate, or tautomer thereof, or any combination thereof which is obtained in (i); and (iii) converting a chiral center of compound (VIII) or a salt, hydrate, or tautomer thereof, or any combination thereof which is obtained in (ii) to form the Compound (XI) or salt, hydrate, or tautomer thereof, or combination thereof.

[45] A process for preparing a compound, which is 2-(1-azabicyclo[2.2.2]oct-2-yl)-6-(3-methyl-1H-pyrazol-4-yl)thieno[3,2-d]pyrimidin-4(3H)-one dihydrochloride, represented as Compound (VII):

(VII)

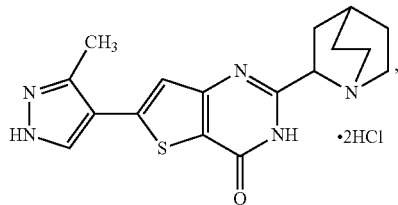

or a hydrate or tautomer thereof, or any combination thereof, wherein the process comprises:
deprotecting a compound represented as Compound (XXI):

(XXI)

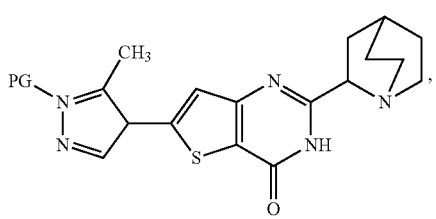

or a salt, hydrate, or tautomer thereof, or any combination thereof in a first reaction mixture, wherein PG is an amine protecting group, to form the 2-(1-azabicyclo[2.2.2]oct-2-yl)-6-(3-methyl-1H-pyrazol-4-yl)thieno[3,2-d]pyrimidin-4(3H)-one as Compound (VIII):

(VIII)

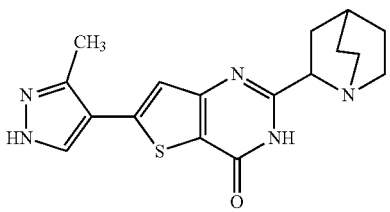

or a salt, hydrate, or tautomer thereof, or any combination thereof; and
treating the first reaction mixture with hydrogen chloride to form a second reaction mixture.

[46] The process according to [45], wherein the deprotecting of the Compound (XXI), or salt, hydrate, or tautomer thereof, or combination thereof, comprises adding a strong acid to the first reaction mixture.

[47] The process according to [46], wherein the strong acid comprises methanesulfonic acid.

[48] The process according to [45], wherein the amine protecting group is p-methoxybenzyl.

[49] A process for preparing a compound, which is 2-(1-azabicyclo[2.2.2]oct-2-yl)-6-(3-methyl-1H-pyrazol-4-yl)thieno[3,2-d]pyrimidin-4(3H)-one, represented as Compound (VIII):

(VIII)

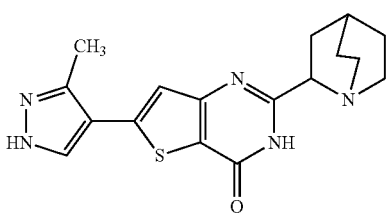

or a salt, hydrate, or tautomer thereof, or any combination thereof, wherein the process comprises:

deprotecting a compound represented as Compound (XXI):

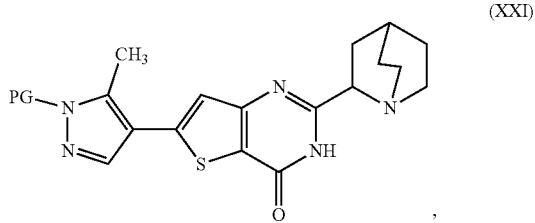

(XXI)

or a salt, hydrate, or tautomer thereof, or any combination thereof in a first reaction mixture, wherein PG is an amine protecting group;

treating the first reaction mixture with hydrogen chloride to form a second reaction mixture comprising a compound which is 2-(1-azabicyclo[2.2.2]oct-2-yl)-6-(3-methyl-1H-pyrazol-4-yl) thieno[3,2-d] pyrimidin-4 (3H)-one dihydrochloride, represented as Compound (VII):

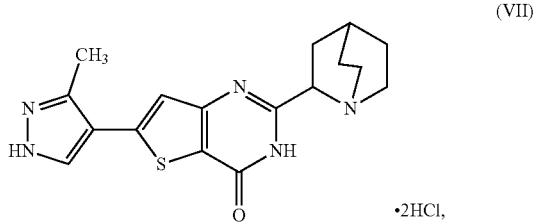 [SMILES: Cc1n[nH]cc1-c1cc2nc(C3CC4CCN3CC4)[nH]c(=O)c2s1]

(VII)

or a hydrate or tautomer thereof, or any combination thereof; and adding a base to the second reaction mixture to form a third reaction mixture.

[50] The process according to [49], wherein the deprotecting of the Compound (XXI) comprises adding a strong acid to the first reaction mixture.

[51] The process according to [50], wherein the strong acid comprises methanesulfonic acid.

[52] The process according to [49], wherein the amine protecting group is p-methoxybenzyl.

[53] The process according to [49], wherein the deprotecting of the Compound (XXI) or salt, hydrate, or tautomer thereof, or combination thereof comprises forming a first reaction mixture by adding methanesulfonic acid and anisole to a mixture of 2-(1-azabicyclo[2.2.2]oct-2-yl)-6-[1-(4-methoxybenzyl)-5-methyl-1H-pyrazol-4-yl]thieno[3,2-d]pyrimidin-4(3H)-one, represented as Compound (VI):

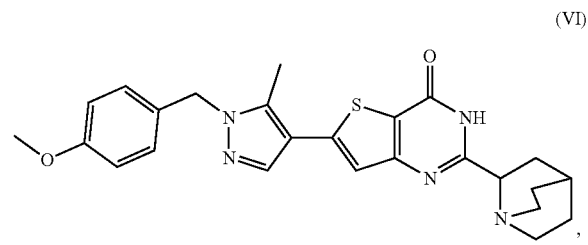 [SMILES: COc1ccc(Cn2ncc(-c3cc4nc(C5CC6CCN5CC6)[nH]c(=O)c4s3)c2C)cc1]

(VI)

dissolved in acetic acid.

[54] The process according to [53], wherein the methanesulfonic acid and the anisole are added at a temperature in a range of about 60° C. or lower.

[55] The process according to [54], wherein the methanesulfonic acid and the anisole are added at a temperature in a range selected from the group consisting of a range between about 20° C. and about 60° C. and a range between about 40° C. and about 60° C.

[56] The process according to [53], further comprising stirring the reaction mixture at a temperature in a range selected from the group consisting of a range between about 85° C. and about 115° C., a range between about 95° C. and about 115° C., and a range between about 105° C. and about 115° C.

[57] The process according to [53], wherein the reaction mixture is stirred for a period selected from the group consisting of a period between about 2 and about 8 hours and a period between about 2 and about 4 hours.

[58] The process according to [53], wherein the first reaction mixture is stirred at a temperature in a range between about 85° C. and about 115° C. for at least 2 hours.

[59] The process according to [53], wherein the deprotecting of the Compound (XXI) further comprises cooling the first reaction mixture to a temperature in a range between about 20° C. and about 60° C.

[60] The process according to [59], wherein the first reaction mixture is cooled to a temperature in a range selected from the group consisting of a range between about 20° C. and about 65° C., a range between about 30° C. and about 60° C., and a range between about 40° C. and about 60° C.

[61] The process according to [49], wherein the treating of the first reaction mixture with hydrogen chloride comprises adding acetonitrile, ethanol, and concentrated hydrochloric acid to the first reaction mixture successively at a temperature in a range between about 20° C. and about 60° C. to form a second reaction mixture.

[62] The process according to [61], wherein the temperature is in a range selected from the group consisting of a range between about 30° C. and about 60° C. and a range between about 40° C. and about 60° C.

[63] The process according to [61], further comprising stirring the second reaction mixture at a temperature in a range selected from the group consisting of a range between about 30° C. and about 60° C. and a range between about 45° C. and about 55° C.

[64] The process according to [63], wherein the second reaction mixture is stirred at the temperature in the range between about 30° C. and about 60° C. for at least 30 minutes.

[65] The process according to [61], further comprising cooling the second reaction mixture to a temperature in a range between about 0° C. and about 30° C.

[66] The process according to [65], wherein the cooled second reaction mixture is stirred for a period selected from the group consisting of a period between about 1 and about 2 hours, a period between about 1 and about 8 hours, and a period between about 1 and about 24 hours.

[67] The process according to [65], further comprising stirring the cooled second reaction mixture for at least 1 hour.

[68] The process according to [61], wherein the treating of the first reaction mixture with hydrogen chloride comprises adding concentrated hydrochloric acid at a temperature of about 50° C.

[69] The process according to [68], further comprising cooling the second reaction mixture to room temperature in about 1 hour.

[70] The process according to [69], wherein the cooled second reaction mixture is stirred for at least 1 hour.

[71] The process according to [70], wherein the cooled second reaction mixture is stirred for a period selected from the group consisting of a period of about 1 hour, a period of about 8 hours, a period of about 16 hours, and a period of about 24 hours.

[72] The process according to [49], wherein the base comprises a potassium carbonate solution.

[73] The process according to [49], wherein the third reaction mixture is stirred at a temperature in a range between about 20° C. and about 85° C. for at least 1 hour.

[74] The process according to [73], wherein the temperature is in a range selected from the group consisting of a range between about 20° C. and about 85° C., a range between about 50° C. and about 85° C., and a range between about 75° C. and about 85° C.

[75] The process according to [73], wherein the third reaction mixture is stirred for a period selected from the group consisting of a period between about 1 and about 2 hours, a period between about 1 and about 8 hours, and a period between about 1 and about 24 hours.

[75'] A process for preparing a compound, which is 2-[(2S)-1-azabicyclo[2.2.2]oct-2-yl]-6-(3-methyl-1H-pyrazol-4-yl)thieno[3,2-d]pyrimidin-4(3H)-one, represented as Compound (XI):

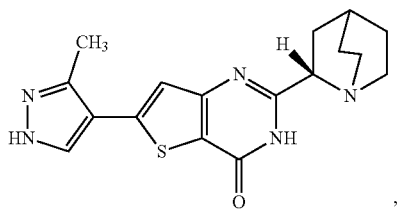

(XI)

or a salt, hydrate, or tautomer thereof, or any combination thereof, the process comprising
(i') deprotecting a compound represented as Compound (XXI):

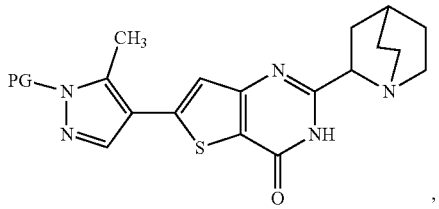

(XXI)

or a salt, hydrate, or tautomer thereof, or any combination thereof in a first reaction mixture, wherein PG is an amine protecting group;

treating the first reaction mixture with hydrogen chloride to form a second reaction mixture comprising a compound which is 2-(l-azabicyclo[2.2.2]oct-2-yl)-6-(3-methyl-1H-pyrazol-4-yl)thieno[3,2-d]pyrimidin-4(3H)-one dihydrochloride, represented as Compound (VII):

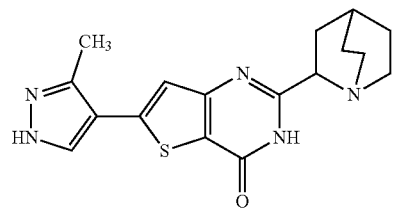

(VII)

·2HCl, or a hydrate or tautomer thereof, or any combination thereof; and adding a base to the second reaction mixture to form a third reaction mixture; and (ii') converting a chiral center of compound (VIII) or a salt, hydrate, or tautomer thereof, or any combination thereof which is obtained as a resultant of (i') to form the Compound (XI) or salt, hydrate, or tautomer thereof, or combination thereof.

[76] A process for preparing a compound, which is methyl 3-amino-5-[1-(4-methoxybenzyl)-5-methyl-1H-pyrazol-4-yl]thiophene-2-carboxylate, represented as Compound (IV):

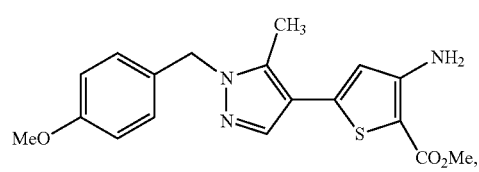

(IV)

or a salt, hydrate, or tautomer thereof, or any combination thereof, the process comprising: reacting 3-(1-(4-methoxybenzyl)-5-methyl-1H-pyrazol-4-yl)-3-oxopropanenitrile, represented as Compound (I):

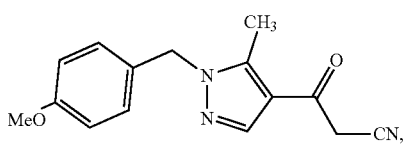

(I)

or a salt, hydrate, or tautomer thereof, or any combination thereof.

[77] The process according to [76], further comprising treating 3-(1-(4-methoxybenzyl)-5-methyl-1H-pyrazol-4-yl)-3-oxopropanenitrile as the Compound (I), or salt, hydrate, or tautomer thereof, or combination thereof with p-toluenesulfonic anhydride or trifluoromethanesulfonic anhydride and a first base at a temperature below about 25° C. to form a first reaction mixture, and wherein the first base comprises triethylamine.

[78] The process according to [76], further comprising: treating 3-(1-(4-methoxybenzyl)-5-methyl-1H-pyrazol-4-yl)-3-oxopropanenitrile as the Compound (I), or salt, hydrate, or tautomer thereof, or combination thereof with p-toluenesulfonic anhydride and a first base at below about 25° C. to form a first reaction mixture, and wherein the first base comprises triethylamine.

[79] The process according to [77], wherein the first reaction mixture is stirred for at least 1 hour.

[80] The process according to [79] wherein the first reaction mixture is stirred for a period selected from the group consisting of a period of about 1 hour, a period of about 8 hours, a period of about 16 hours, and a period of about 24 hours.

[81] The process according to [77], further adding a second base in the treating of the Compound (I), or salt, hydrate, or tautomer thereof, or combination thereof, wherein the second base comprises potassium hydroxide, sodium hydroxide, or lithium hydroxide to form a second reaction mixture.

[82] The process according to [81], wherein the second base comprises potassium hydroxide.

[83] The process according to [81], wherein the second reaction mixture is stirred for a period between about 1 and about 24 hours.

[84] The process according to [81], further comprising adding ammonium chloride and adjusting pH of the second reaction mixture until the pH reaches pH in a range between 7 and 10 to form a third reaction mixture.

[85] The process according to [84], further comprising adding methyl thioglycolate to the third reaction mixture to form a fourth reaction mixture.

[86] The process according to [85], wherein the fourth reaction mixture is stirred for a period between about 1 and about 24 hours at about 25° C.

[87] The process according to [86], further comprising adding a third base to the fourth reaction mixture to form a fifth reaction mixture, wherein the third base comprises 1,8-diazabicycloundec-7-ene or 1,5-diazabicyclo(4.3.0)non-5-ene.

[88] The process according to [87], wherein the third base comprises 1,8-diazabicycloundec-7-ene.

[89] The process according to [87], wherein the fifth reaction mixture is stirred for a period between about 1 and about 24 hours at about 25° C.

[90] The process according to [87], further comprising adding water to the fifth reaction mixture.

[91] The process according to [90], further comprising adding a seed crystal of methyl 3-amino-5-[1-(4-methoxybenzyl)-5-methyl-1H-pyrazol-4-yl]thiophene-2-carboxylate as the Compound (IV), or a salt, hydrate, or tautomer thereof, or any combination thereof to the fifth reaction mixture and the water.

[92] The process according to [91], further comprising adding water to the fifth reaction mixture, the water, and the seed crystal over a period of 3 hours to form a sixth reaction mixture.

[93] The process according to [92], further comprising aging the sixth reaction mixture for a period between about 1 and about 18 hours at about 25° C.

[94] The process according to [93], further comprising collecting solids of the aged sixth reaction mixture by filtration.

[95] The process according to [94], further comprising washing the solids at least with tetrahydrofuran and water.

[96] The process according to [76], further comprising preparing 2-[(2S)-1-azabicyclo[2.2.2]oct-2-yl]-6-(3-methyl-1H-pyrazol-4-yl)thieno[3,2-d]pyrimidin-4(3H)-one, represented as Compound (XI):

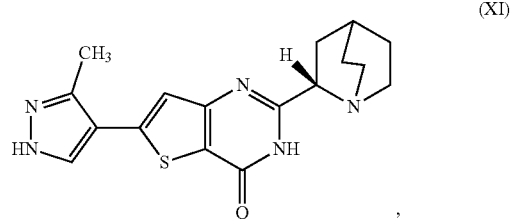 [SMILES: Cc1n[nH]cc1-c1cc2nc([C@@H]3CC4CCN3CC4)[nH]c(=O)c2s1]

or a salt, hydrate, or tautomer thereof, or any combination thereof, from a mixture comprising methyl 3-amino-5-[1-(4-methoxybenzyl)-5-methyl-1H-pyrazol-4-yl]thiophene-2-carboxylate as the compound (IV):

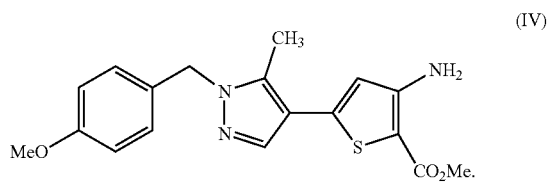 [SMILES: COC(=O)c1sc(-c2cnn(Cc3ccc(OC)cc3)c2C)cc1N]

[96'] The process according to [96], wherein the 2-[(2S)-1-azabicyclo[2.2.2]oct-2-yl]-6-(3-methyl-1H-pyrazol-4-yl)thieno[3,2-d]pyrimidin-4(3H)-one, as Compound (XI):

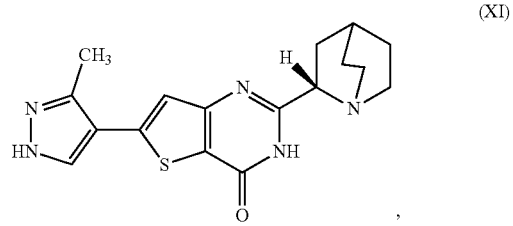 [SMILES: Cc1n[nH]cc1-c1cc2nc([C@@H]3CC4CCN3CC4)[nH]c(=O)c2s1]

or salt, hydrate, or tautomer thereof, or combination thereof is 2-[(2S)-1-azabicyclo[2.2.2]oct-2-yl]-6-(3-methyl-1H-pyrazol-4-yl)thieno[3,2-d]pyrimidin-4(3H)-one hemihydrate or a tautomer thereof, or any combination thereof.

[96"] A process for preparing a compound, which is 2-[(2S)-1-azabicyclo[2.2.2]oct-2-yl]-6-(3-methyl-1H-pyrazol-4-yl)thieno[3,2-d]pyrimidin-4(3H)-one, represented as Compound (XI):

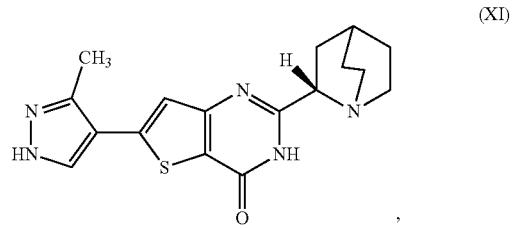 [SMILES: Cc1n[nH]cc1-c1cc2nc([C@@H]3CC4CCN3CC4)[nH]c(=O)c2s1]

or a salt, hydrate, or tautomer thereof, or any combination thereof, the process comprising reacting 3-(1-(4-methoxybenzyl)-5-methyl-1H-pyrazol-4-yl)-3-oxopropanenitrile, represented as Compound (I):

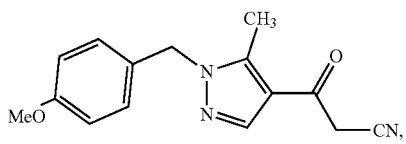
(I)

or a salt, hydrate, or tautomer thereof, or any combination thereof.

[97] A compound, which is 3-(1-(4-methoxybenzyl)-5-methyl-1H-pyrazol-4-yl)-3-oxopropanenitrile, represented as Compound (I):

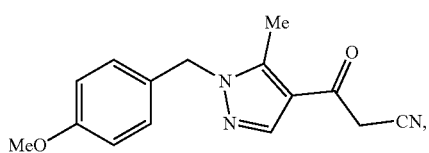
(I)

or a salt, hydrate, or tautomer thereof, or any combination thereof.

[98] A compound, which is (2S,3S)-2,3-bis(benzoyloxy)butanedioic acid 2-[(2S)-1-azabicyclo[2.2.2]oct-2-yl]-6-(3-methyl-1H-pyrazol-4-yl)thieno[3,2-d]pyrimidin-4(3H)-one, represented as Compound(IX):

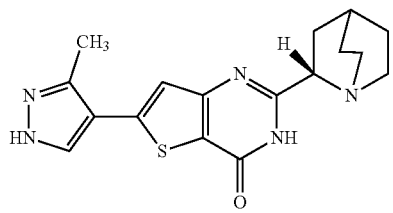
(IX)

or a salt, hydrate, or tautomer thereof, or any combination thereof.

[99] A compound which is 5-(1-(4-Methoxybenzyl)-5-methyl-1H-pyrazol-4-yl)-3-(quinuclidine-2-carboxamido)thiophene-2-carboxylic acid, represented as Compound (XXIV):

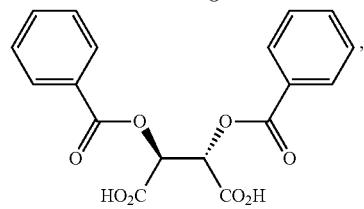
(XXIV)

or a salt or hydrate thereof.

[100] (A compound (XXV) having a structure:

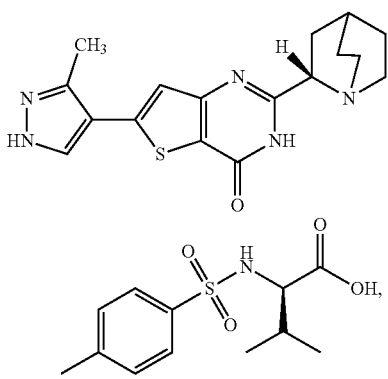
(XXV)

or a tautomer thereof.

[101] A process for preparing a compound, which is 2-[(2S)-1-azabicyclo[2.2.2]oct-2-yl]-6-(3-methyl-1H-pyrazol-4-yl)thieno[3,2-d]pyrimidin-4(3H)-one, represented as Compound (XI):

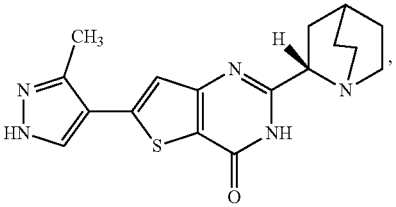
(XI)

or a salt, hydrate, or tautomer thereof, or any combination thereof, the process comprising:

reacting methyl 3-amino-5-[1-(4-methoxybenzyl)-5-methyl-1H-pyrazol-4-yl]thiophene-2-carboxylate, represented as Compound (IV):

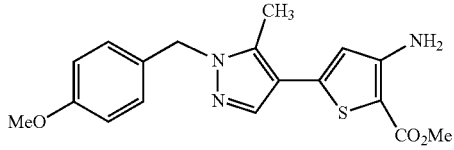
(IV)

or a salt, hydrate, or tautomer thereof, or any combination thereof to form methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate, represented as Compound (V):

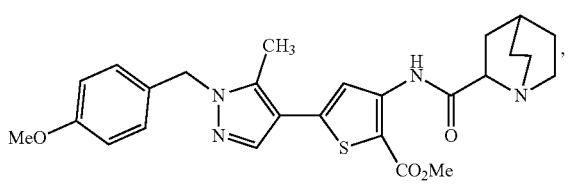
(V)

or a salt, hydrate, or tautomer thereof, or any combination thereof; and reacting the methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate as the Compound (V) or salt, hydrate, or tautomer thereof, or combination thereof to form 2-(1-azabicyclo[2.2.2]oct-2-yl)-6-[1-(4-methoxybenzyl)-5-methyl-1H-pyrazol-4-yl]thieno[3,2-d]pyrimidin-4(3H)-one, represented as Compound(VI):

(VI)

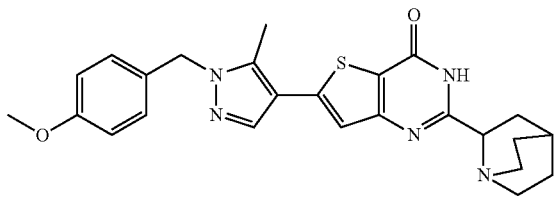

or a salt, hydrate, or tautomer thereof, or any combination thereof, reacting the 2-(1-azabicyclo[2.2.2]oct-2-yl)-6-[1-(4-methoxybenzyl)-5-methyl-1H-pyrazol-4-yl]thieno[3,2-d]pyrimidin-4(3H)-one as the Compound (VI), or salt, hydrate, or tautomer thereof, or combination thereof, to form 2-(1-azabicyclo[2.2.2]oct-2-yl)-6-(3-methyl-1H-pyrazol-4-yl)thieno[3,2-d]pyrimidin-4(3H)-one, represented as Compound (VIII):

(VIII)

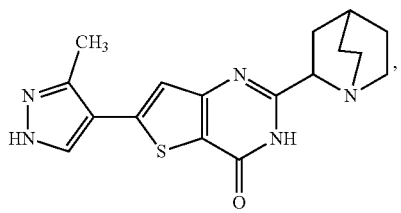

or a salt, hydrate, or tautomer thereof, or any combination thereof;
and reacting the 2-(1-azabicyclo[2.2.2]oct-2-yl)-6-(3-methyl-1H-pyrazol-4-yl)thieno[3,2-d]pyrimidin-4(3H)-one as the Compound (VIII), or salt, hydrate, or tautomer thereof, or combination thereof, to form the 2-[(2S)-1-azabicyclo[2.2.2]oct-2-yl]-6-(3-methyl-1H-pyrazol-4-yl)thieno[3,2-d]pyrimidin-4(3H)-one as the Compound (XI), or salt, hydrate, or tautomer thereof, or combination thereof.

[101'] The process according to [101], wherein the 2-[(2S)-1-azabicyclo[2.2.2]oct-2-yl]-6-(3-methyl-1H-pyrazol-4-yl)thieno[3,2-d]pyrimidin-4(3H)-one as the Compound (XI), or salt, hydrate, or tautomer thereof, or combination thereof is 2-[(2S)-1-azabicyclo[2.2.2]oct-2-yl]-6-(3-methyl-1H-pyrazol-4-yl)thieno[3,2-d]pyrimidin-4(3H)-one hemihydrate or a tautomer thereof, or any combination thereof.

[102] The process according to [101], wherein the reacting of methyl 3-amino-5-[1-(4-methoxybenzyl)-5-methyl-1H-pyrazol-4-yl]thiophene-2-carboxylate as the Compound (IV), or salt, hydrate, or tautomer thereof, or combination thereof, to form the methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate as the Compound (V), or salt, hydrate, or tautomer thereof, or combination thereof comprises:

forming a reaction mixture comprising: quinuclidine-2-carboxylic acid hydrochloride, acetonitrile, dimethyl formamide, oxalyl chloride, and methyl 3-amino-5-[1-(4-methoxybenzyl)-5-methyl-1H-pyrazol 4-yl]thiophene-2-carboxylate as the Compound (IV), or salt, hydrate, or tautomer thereof, or combination thereof.

In the reaction mixture, other coupling reagents in amide synthesis may be used instead of oxalyl chloride. Examples of the "coupling reagents in amide synthesis" in the present specification include 1,1-carbonyldiimidazole (CDI), 1-ethyl-3-(3-dimethylaminopropyl)carbodiimide (EDCI), O-(7-azabenzotriazol-1-yl)-N,N,N',N'-tetramethyluronium hexafluorophosphate (HATU), 2-(1H-benzotriazol-1-yl)-1,1,3,3-tetramethyluronium hexafluorophosphate (HBTU), 2-(1H-benzotriazole-1-yl)-1,1,3,3-tetramethylaminium tetrafluoroborate (TBTU), n-propanephosphonic acid anhydride (T3P).

[103] The process according to [101], wherein the reacting of the methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate as the Compound (V) or salt, hydrate, or tautomer thereof, or combination thereof, to form the 2-(1-azabicyclo[2.2.2]oct-2-yl)-6-[1-(4-methoxybenzyl)-5-methyl-1H-pyrazol-4-yl]thieno[3,2-d]pyrimidin-4(3H)-one as the Compound (VI) or salt, hydrate, or tautomer thereof, or combination thereof comprises:

forming a reaction mixture comprising: methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate as the Compound (V) or salt, hydrate, tautomer or combination thereof;
dimethyl acetamide or acetamide or a combination thereof; and potassium tert-butoxide.

[104] The process according to [101], wherein the reacting of the 2-(1-azabicyclo[2.2.2]oct-2-yl)-6-[1-(4-methoxybenzyl)-5-methyl-1H-pyrazol-4-yl]thieno[3,2-d]pyrimidin-4(3H)-one as the Compound (VI), or salt, hydrate, or tautomer thereof, or combination thereof to form the 2-(1-azabicyclo[2.2.2]oct-2-yl)-6-(3-methyl-1H-pyrazol-4-yl)thieno[3,2-d]pyrimidin-4(3H)-one, as the Compound (VIII) or salt, hydrate, or tautomer thereof, or combination thereof comprises:

forming a reaction mixture comprising:
2-(1-azabicyclo[2.2.2]oct-2-yl)-6-[1-(4-methoxybenzyl)-5-methyl-1H-pyrazol-4-yl]thieno[3,2-d]pyrimidin-4(3H)-one as the Compound (VI), or salt, hydrate, or tautomer thereof, or combination thereof,
acetic acid,
methanesulfonic acid, and
anisole;
adding materials comprising acetonitrile, ethyl alcohol, and hydrochloric acid to the reaction mixture in combinations or separately;
filtering solids from the reaction mixture;
washing the solids with at least acetonitrile; and
forming a second reaction mixture comprising the washed solids, potassium carbonate, and water.

[105] The process according to [101] or [101'], wherein the reacting of the 2-(1-azabicyclo[2.2.2]oct-2-yl)-6-(3-methyl-1H-pyrazol-4-yl)thieno[3,2-d]pyrimidin-4(3H)-one as the Compound (VIII), or salt, hydrate, or tautomer thereof, or combination thereof, to form the 2-[(2S)-1-azabicyclo[2.2.2]oct-2-yl]-6-(3-methyl-1H-pyrazol-4-yl)thieno[3,2-d]pyrimidin-4(3H)-one as the Compound (XI) or salt, hydrate, or tautomer thereof, or combination thereof comprises:

forming a first reaction mixture comprising:
2-(1-azabicyclo[2.2.2]oct-2-yl)-6-(3-methyl-1H-pyrazol-4-yl)thieno[3,2-d]pyrimidin-4(3H)-one as the Compound (VIII), or salt, hydrate, or tautomer thereof, or combination thereof,
(2S,3S)-2,3-bis(benzoyloxy)butanedioic acid monohydrate, at least one compound selected from the group consisting of 1-butanol and 2-butanol, and at least one compound selected from the group consisting of ethyl acetate and acetic acid; and forming a second reaction mixture comprising:

(2S,3S)-2,3-bis(benzoyloxy)butanedioic acid 2-[(2S)-1-azabicyclo[2.2.2]oct-2-yl]-6-(3-methyl-1H-pyrazol-4-yl)thieno[3,2-d]pyrimidin-4(3H)-one, represented as Compound (IX):

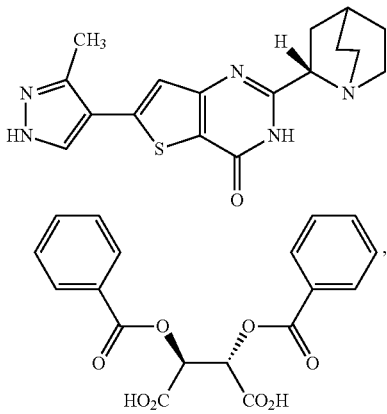

(IX)

or a salt, hydrate, or tautomer thereof, or any combination thereof, acetone, water, and aqueous ammonium hydroxide.

[106] A process for preparing a compound, which is 2-[(2S)-1-azabicyclo[2.2.2]oct-2-yl]-6-(3-methyl-1H-pyrazol-4-yl)thieno[3,2-d]pyrimidin-4(3H)-one, represented as Compound (XI):

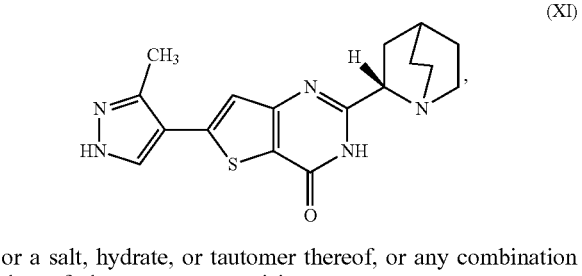

(XI)

or a salt, hydrate, or tautomer thereof, or any combination thereof, the process comprising:

reacting 2-(1-azabicyclo[2.2.2]oct-2-yl)-6-[1-(4-methoxybenzyl)-5-methyl-1H-pyrazol-4-yl]thieno[3,2-d]pyrimidin-4(3H)-one, represented as Compound (VI):

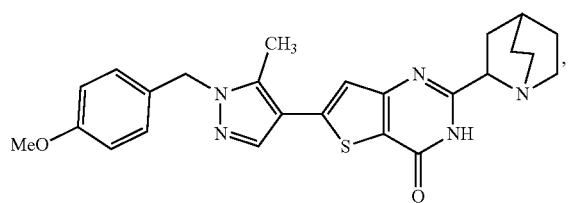

(VI)

or a salt, hydrate, or tautomer thereof, or any combination thereof, to form 2-(1-azabicyclo[2.2.2]oct-2-yl)-6-(3-methyl-1H-pyrazol-4-yl)thieno[3,2-d]pyrimidin-4(3H)-one, represented as Compound (VIII):

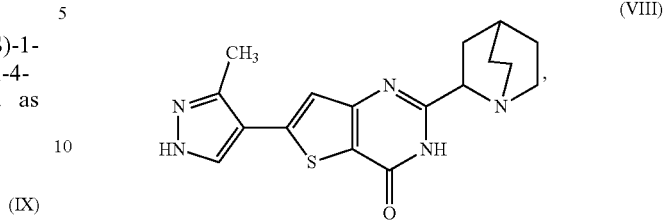

(VIII)

or a salt, hydrate, or tautomer thereof, or any combination thereof; and reacting the 2-(1-azabicyclo[2.2.2]oct-2-yl)-6-(3-methyl-1H-pyrazol-4-yl)thieno[3,2-d]pyrimidin-4(3H)-one as the Compound (VIII), or salt, hydrate, or tautomer thereof, or combination thereof to form the 2-[(2S)-1-azabicyclo[2.2.2]oct-2-yl]-6-(3-methyl-1H-pyrazol-4-yl)thieno[3,2-d]pyrimidin-4(3H)-one as the Compound (XI), or salt, hydrate, or tautomer thereof, or combination thereof.

[106'] The process according to [106], wherein the 2-[(2S)-1-azabicyclo[2.2.2]oct-2-yl]-6-(3-methyl-1H-pyrazol-4-yl)thieno[3,2-d]pyrimidin-4(3H)-one as the Compound (XI), or salt, hydrate, or tautomer thereof, or combination thereof is 2-[(2S)-1-azabicyclo[2.2.2]oct-2-yl]-6-(3-methyl-1H-pyrazol-4-yl)thieno[3,2-d]pyrimidin-4(3H)-one hemihydrate or a tautomer thereof, or any combination thereof.

[107] The process according to [106], wherein the reacting of the 2-(1-azabicyclo[2.2.2]oct-2-yl)-6-[1-(4-methoxybenzyl)-5-methyl-1H-pyrazol-4-yl]thieno[3,2-d]pyrimidin-4(3H)-one as the Compound (VI), or salt, hydrate, or tautomer thereof, or combination thereof, to form the 2-(1-azabicyclo[2.2.2]oct-2-yl)-6-(3-methyl-1H-pyrazol-4-yl)thieno[3,2-d]pyrimidin-4(3H)-one, as Compound (VIII) or salt, hydrate, or tautomer thereof, or combination thereof comprises:

forming a reaction mixture comprising:
2-(1-azabicyclo[2.2.2]oct-2-yl)-6-[1-(4-methoxybenzyl)-5-methyl-1H-pyrazol-4-yl]thieno[3,2-d]pyrimidin-4(3H)-one as the Compound (VI), or salt, hydrate, or tautomer thereof, or combination thereof, acetic acid, methanesulfonic acid, and anisole;

adding materials comprising acetonitrile, ethyl alcohol, and hydrochloric acid to the reaction mixture, in combinations or separately;

filtering solids from the reaction mixture;

washing the solids with at least acetonitrile; and forming a second reaction mixture comprising the washed solids, potassium carbonate, and water.

[108] The process according to [106] or [106'], wherein the reacting of the 2-(1-azabicyclo[2.2.2]oct-2-yl)-6-(3-methyl-1H-pyrazol-4-yl)thieno[3,2-d]pyrimidin-4(3H)-one as the Compound (VIII), or salt, hydrate, or tautomer thereof, or combination thereof, to form the 2-[(2S)-1-azabicyclo[2.2.2]oct-2-yl]-6-(3-methyl-1H-pyrazol-4-yl)thieno[3,2-d]pyrimidin-4(3H)-one as the Compound (XI) or salt, hydrate, or tautomer thereof, or combination thereof comprises:

forming a first reaction mixture comprising:
2-(1-azabicyclo[2.2.2]oct-2-yl)-6-(3-methyl-1H-pyrazol-4-yl)thieno[3,2-d]pyrimidin-4(3H)-one as the Compound (VIII), or salt, hydrate, or tautomer thereof, or combination thereof, (2S,3S)-2,3-bis(benzoyloxy)butanedioic acid monohydrate,
at least one compound selected from the group consisting of 1-butanol and 2-butanol, and
acetic acid, and
forming a second reaction mixture comprising:
(2S,3S)-2,3-bis(benzoyloxy)butanedioic acid 2-[(2S)-1-azabicyclo[2.2.2]oct-2-yl]-6-(3-methyl-1H-pyrazol-4-yl)thieno[3,2-d]pyrimidin-4(3H)-one, represented as Compound (IX):

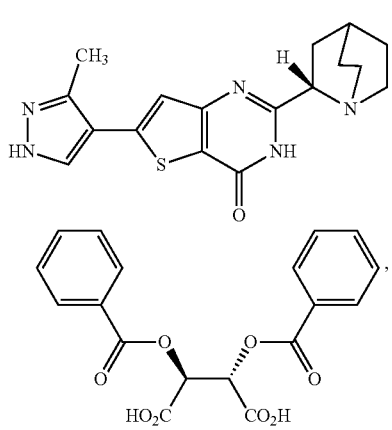

(IX)

or a salt, hydrate, or tautomer thereof, or any combination thereof,
acetone,
water, and
aqueous ammonium hydroxide.

[109] A process for preparing a compound, which is methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate, represented as Compound (V):

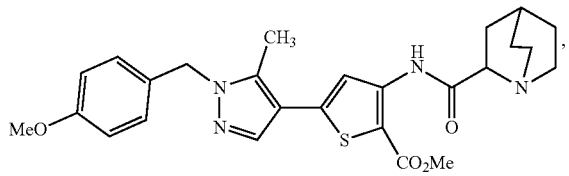

(V)

or a salt, hydrate, or tautomer thereof, or any combination thereof, the process comprising:
reacting a compound, which is methyl 3-amino-5-[1-(4-methoxybenzyl)-5-methyl-1H-pyrazol-4-yl]thiophene-2-carboxylate, represented as Compound (IV):

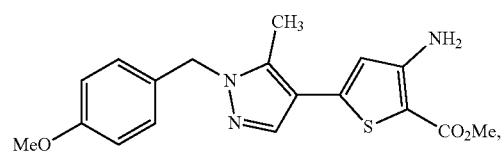

(IV)

or a salt, hydrate, or tautomer thereof, or any combination thereof to form the methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate, as the Compound (V), or a salt, hydrate, or tautomer thereof, or any combination thereof.

[110] The process according to [109], wherein the reacting of the methyl 3-amino-5-[1-(4-methoxybenzyl)-5-methyl-1H-pyrazol-4-yl]thiophene-2-carboxylate as the Compound (IV), or salt, hydrate, or tautomer thereof, or any combination thereof to form the methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate, as the Compound (V), or salt, hydrate, or tautomer thereof, or combination thereof comprises:
forming a reaction mixture comprising:
quinuclidine-2-carboxylic acid hydrochloride,
acetonitrile,
dimethyl formamide,
oxalyl chloride, and
methyl 3-amino-5-[1-(4-methoxybenzyl)-5-methyl-1H-pyrazol-4-yl]thiophene-2-carboxylate as the Compound (IV), or a salt, hydrate, or tautomer thereof, or combination thereof.

[111] A process for preparing a compound, which is 2-[(2S)-1-azabicyclo[2.2.2]oct-2-yl]-6-(3-methyl-1H-pyrazol-4-yl)thieno[3,2-d]pyrimidin-4(3H)-one, represented as Compound (XI):

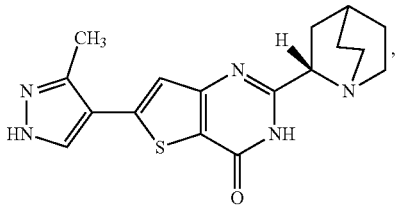

(XI)

or a salt, hydrate, or tautomer thereof, or any combination thereof, the process comprising:
reacting 3-(1-(4-methoxybenzyl)-5-methyl-1H-pyrazol-4-yl)-3-oxopropanenitrile, represented as Compound (I):

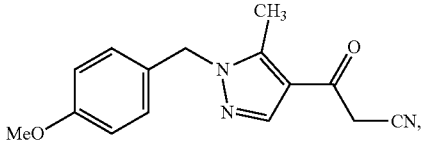

(I)

or a salt, hydrate, or tautomer thereof, or any combination thereof to form 2-(1-azabicyclo[2.2.2]oct-2-yl)-6-(3-methyl-1H-pyrazol-4-yl)thieno[3,2-d]pyrimidin-4(3H)-one, represented as Compound (IV):

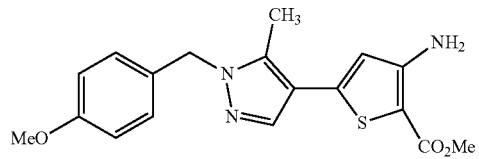

(IV)

or a salt, hydrate, or tautomer thereof, or any combination thereof;

reacting the 2-(1-azabicyclo[2.2.2]oct-2-yl)-6-(3-methyl-1H-pyrazol-4-yl)thieno[3,2-d]pyrimidin-4(3H)-one as the Compound (IV), or salt, hydrate, or tautomer thereof, or combination thereof to form methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate, represented as Compound (V):

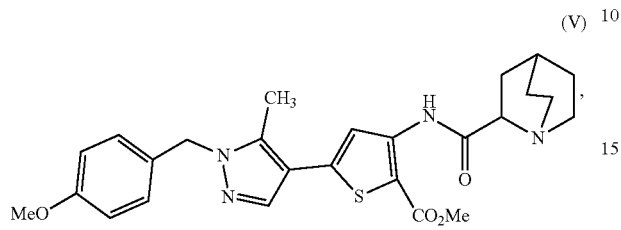

or a salt, hydrate, or tautomer thereof, or any combination thereof;

reacting the methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate as the Compound (V), or salt, hydrate, or tautomer thereof, or combination thereof to form 2-(1-azabicyclo[2.2.2]oct-2-yl)-6-[1-(4-methoxybenzyl)-5-methyl-1H-pyrazol-4-yl]thieno[3,2-d]pyrimidin-4(3H)-one, represented as Compound (VI):

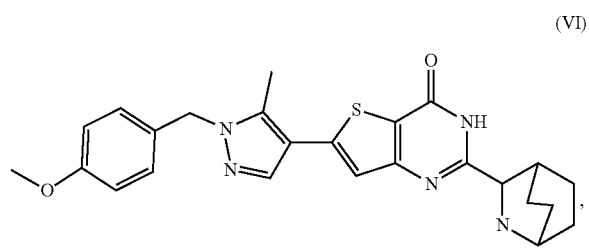 [SMILES: COc1ccc(Cn2ncc(-c3cc4nc(C5NC6CCC5CC6)[nH]c(=O)c4s3)c2C)cc1]

or a salt, hydrate, or tautomer thereof, or any combination thereof;

reacting the 2-(1-azabicyclo[2.2.2]oct-2-yl)-6-[1-(4-methoxybenzyl)-5-methyl-1H-pyrazol-4-yl]thieno[3,2-d]pyrimidin-4(3H)-one as the Compound (VI), or salt, hydrate, or tautomer thereof, or combination thereof to form 2-(1-azabicyclo[2.2.2]oct-2-yl)-6-(3-methyl-1H-pyrazol-4-yl)thieno[3,2-d]pyrimidin-4(3H)-one, represented as Compound (VIII):

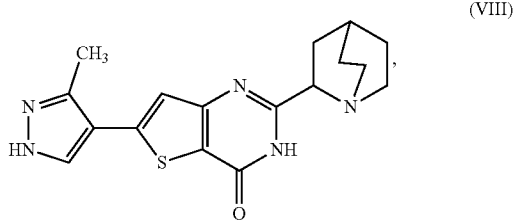 [SMILES: Cc1n[nH]cc1-c1cc2nc(C3CC4CCN3CC4)[nH]c(=O)c2s1]

or a salt, hydrate, or tautomer thereof, or any combination thereof;

reacting the 2-(1-azabicyclo[2.2.2]oct-2-yl)-6-(3-methyl-1H-pyrazol-4-yl)thieno[3,2-d]pyrimidin-4(3H)-one as the Compound (VIII), or salt, hydrate, or tautomer thereof, or combination thereof to form (2S,3S)-2,3-bis(benzoyloxy)butanedioic acid 2-[(2S)-1-azabicyclo[2.2.2]oct-2-yl]-6-(3-methyl-1H-pyrazol-4-yl)thieno[3,2-d]pyrimidin-4(3H)-one, represented as Compound (IX):

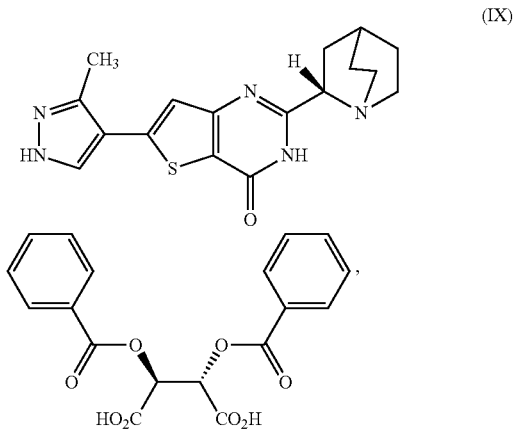

or a salt, hydrate, or tautomer thereof, or any combination thereof; and reacting the (2S,3S)-2,3-bis(benzoyloxy)butanedioic acid 2-[(2S)-1-azabicyclo[2.2.2]oct-2-yl]-6-(3-methyl-1H-pyrazol-4-yl)thieno[3,2-d]pyrimidin-4(3H)-one as the Compound (IX), or salt, hydrate, or tautomer thereof, or combination thereof to form the 2-[(2S)-1-azabicyclo[2.2.2]oct-2-yl]-6-(3-methyl-1H-pyrazol-4-yl)thieno[3,2-d]pyrimidin-4(3H)-one as the Compound (XI), or salt, hydrate, or tautomer thereof, or combination thereof.

[111'] The process according to [111], wherein the 2-[(2S)-1-azabicyclo[2.2.2]oct-2-yl]-6-(3-methyl-1H-pyrazol-4-yl)thieno[3,2-d]pyrimidin-4(3H)-one as the Compound (XI), or salt, hydrate, or tautomer thereof, or combination thereof is 2-[(2S)-1-azabicyclo[2.2.2]oct-2-yl]-6-(3-methyl-1H-pyrazol-4-yl)thieno[3,2-d]pyrimidin-4(3H)-one hemihydrate or a tautomer thereof, or any combination thereof.

[112] The process according to [111], wherein the reacting 3-(1-(4-methoxybenzyl)-5-methyl-1H-pyrazol-4-yl)-3-oxopropanenitrile, as the Compound (I), or salt, hydrate, or tautomer thereof, or combination thereof to form the 2-(1-azabicyclo[2.2.2]oct-2-yl)-6-(3-methyl-1H-pyrazol-4-yl)thieno[3,2-d]pyrimidin-4(3H)-one, as the Compound (IV) or salt, hydrate, or tautomer thereof, or combination thereof comprises:

forming a reaction mixture comprising:
3-(1-(4-methoxybenzyl)-5-methyl-1H-pyrazol-4-yl)-3-oxopropanenitrile, as the Compound (I) or salt, hydrate, or tautomer thereof, or combination thereof,
p-toluenesulfonic anhydride,
anhydrous tetrahydrofuran, and
trimethylamine;
adding a material comprising potassium hydroxide to the reaction mixture; and
adding materials comprising ammonium chloride methyl thioglycolate, and diazabicyclo[5.4.0]undec-7-ene to the reaction mixture in combinations or separately.

[113] The process according to [111], wherein the reacting of the methyl 3-amino-5-[1-(4-methoxybenzyl)-5-methyl-1H-pyrazol-4-yl]thiophene-2-carboxylate as the Compound (IV), or salt, hydrate, or tautomer thereof, or combination thereof to form the methyl 3-[(1-azabicyclo[2.2.2]oct-2- ylcarbonyl)amino]-5-[1-(4-methoxybenzyl)-5-methyl-1H-pyrazol-4-yl]thiophene-2-carboxylate, as the Compound (V), or salt, hydrate, or tautomer thereof, or combination thereof comprises:
  forming a reaction mixture comprising:
    quinuclidine-2-carboxylic acid hydrochloride,
    acetonitrile,
    dimethyl formamide,
    oxalyl chloride, and
    methyl 3-amino-5-[1-(4-methoxybenzyl)-5-methyl-1H-pyrazol 4-yl]thiophene-2-carboxylate as Compound (IV), or salt, hydrate, or tautomer thereof, or combination thereof.

[114] The process according to [111], wherein the reacting of the methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate as the Compound (V), or salt, hydrate, or tautomer thereof, or combination thereof to form 2-(1-azabicyclo[2.2.2]oct-2-yl)-6-[1-(4-methoxybenzyl)-5-methyl-1H-pyrazol-4-yl]thieno[3,2-d]pyrimidin-4(3H)-one as Compound (VI) or salt, hydrate, tautomer or combination thereof comprises:
  forming a reaction mixture comprising:
    methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate as the Compound (V) or salt, hydrate, tautomer or combination thereof,
    dimethyl acetamide or acetamide or a combination thereof, and
    potassium tert-butoxide.

[115] The process according to [111], wherein the reacting of the 2-(1-azabicyclo[2.2.2]oct-2-yl)-6-[1-(4-methoxybenzyl)-5-methyl-1H-pyrazol-4-yl]thieno[3,2-d]pyrimidin-4(3H)-one as the Compound (VI), or salt, hydrate, or tautomer thereof, or combination thereof, to form 2-(1-azabicyclo[2.2.2]oct-2-yl)-6-(3-methyl-1H-pyrazol-4-yl)thieno[3,2-d]pyrimidin-4(3H)-one, as Compound (VIII) or salt, hydrate, or tautomer thereof, or combination thereof comprises:
  forming a reaction mixture comprising:
    2-(1-azabicyclo[2.2.2]oct-2-yl)-6-[1-(4-methoxybenzyl)-5-methyl-1H-pyrazol-4-yl]thieno[3,2-d]pyrimidin-4(3H)-one as the Compound (VI), or salt, hydrate, or tautomer thereof, or combination thereof,
    acetic acid,
    methanesulfonic acid, and
    anisole;
  adding materials comprising acetonitrile, ethyl alcohol, and hydrochloric acid to the reaction mixture in combinations or separately;
  filtering solids from the reaction mixture;
  washing the solids with at least acetonitrile; and
  forming a second reaction mixture comprising the washed solids, potassium carbonate, and water.

[116] The process according to [111] or [111'], wherein the reacting of the 2-(1-azabicyclo[2.2.2]oct-2-yl)-6-(3-methyl-1H-pyrazol-4-yl)thieno[3,2-d]pyrimidin-4(3H)-one as the Compound (VIII), or salt, hydrate, or tautomer thereof, or combination thereof, to form the 2-[(2S)-1-azabicyclo[2.2.2]oct-2-yl]-6-(3-methyl-1H-pyrazol-4-yl)thieno[3,2-d]pyrimidin-4(3H)-one as the Compound (XI) or salt, hydrate, or tautomer thereof, or combination thereof comprises:
  forming a first reaction mixture comprising:
    2-(1-azabicyclo[2.2.2]oct-2-yl)-6-(3-methyl-1H-pyrazol-4-yl)thieno[3,2-d]pyrimidin-4(3H)-one as the Compound (VIII), or salt, hydrate, or tautomer thereof, or combination thereof,
    (2S,3S)-2,3-bis(benzoyloxy)butanedioic acid monohydrate,
    at least one compound selected from the group consisting of 1-butanol and 2-butanol, and
    at least one compound selected from the group consisting of ethyl acetate and acetic acid; and
  forming a second reaction mixture comprising:
    (2S,3S)-2,3-bis(benzoyloxy)butanedioic acid 2-[(2S)-1-azabicyclo[2.2.2]oct-2-yl]-6-(3-methyl-1H-pyrazol-4-yl)thieno[3,2-d]pyrimidin-4(3H)-one, as the Compound (IX):

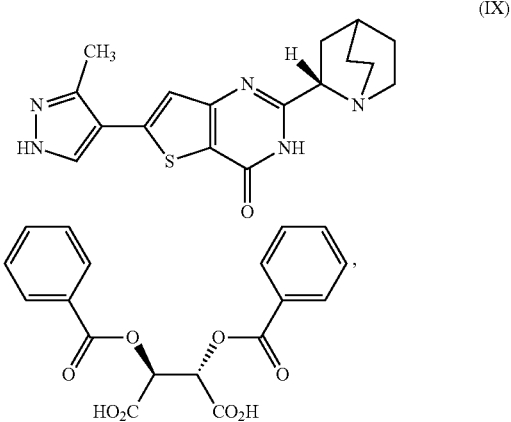

(IX)

or salt, hydrate, or tautomer thereof, or combination thereof,
    acetone,
    water, and
    aqueous ammonium hydroxide.

[117] A process for preparing a compound, which is 2-[(2S)-1-azabicyclo[2.2.2]oct-2-yl]-6-(3-methyl-1H-pyrazol-4-yl)thieno[3,2-d]pyrimidin-4(3H)-one, represented as Compound (XI):

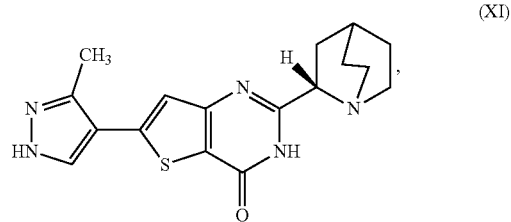 [SMILES: Cc1n[nH]cc1-c1cc2nc([C@@H]3CC4CCN3CC4)[nH]c(=O)c2s1]

(XI)

or a salt, hydrate, or tautomer thereof, or any combination thereof, comprising reacting (2S,3S)-2,3-bis(benzoyloxy)butanedioic acid 2-[(2S)-1-azabicyclo[2.2.2]oct-2-yl]-6-(3-methyl-1H-pyrazol-4-yl)thieno[3,2-d]pyrimidin-4(3H)-one, represented as Compound (IX):

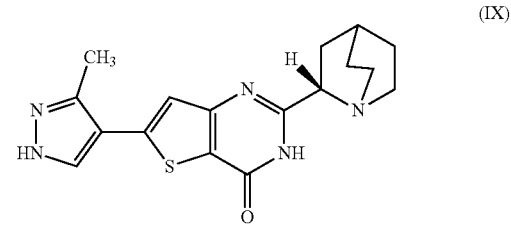

(IX)

-continued or a salt, hydrate, or tautomer thereof, or any combination thereof to form the 2-[(2S)-1-azabicyclo[2.2.2]oct-2-yl]-6-(3-methyl-1H-pyrazol-4-yl)thieno[3,2-d]pyrimidin-4(3H)-one as the Compound (XI), or salt, hydrate, or tautomer thereof, or combination thereof.

[117'] The process according to [117], wherein the 2-[(2S)-1-azabicyclo[2.2.2]oct-2-yl]-6-(3-methyl-1H-pyrazol-4-yl)thieno[3,2-d]pyrimidin-4(3H)-one as the Compound (XI), or salt, hydrate, or tautomer thereof, or combination thereof is 2-[(2S)-1-azabicyclo[2.2.2]oct-2-yl]-6-(3-methyl-1H-pyrazol-4-yl)thieno[3,2-d]pyrimidin-4(3H)-one hemihydrate or a tautomer thereof, or any combination thereof.

[118] The process according to [117] or [117'], wherein the reacting of (2S,3S)-2,3-bis(benzoyloxy)butanedioic acid 2-[(2S)-1-azabicyclo[2.2.2]oct-2-yl]-6-(3-methyl-1H-pyrazol-4-yl)thieno[3,2-d]pyrimidin-4(3H)-one as the Compound (IX), below, or salt, hydrate, or tautomer thereof, or combination thereof to form the 2-[(2S)-1-azabicyclo[2.2.2]oct-2-yl]-6-(3-methyl-1H-pyrazol-4-yl)thieno[3,2-d]pyrimidin-4(3H)-one as the Compound (XI), or salt, hydrate, or tautomer thereof, or combination thereof comprises:

forming a reaction mixture comprising:
(2S,3S)-2,3-bis(benzoyloxy)butanedioic acid 2-[(2S)-1-azabicyclo[2.2.2]oct-2-yl]-6-(3-methyl-1H-pyrazol-4-yl)thieno[3,2-d]pyrimidin-4(3H)-one, as the Compound (IX):

(IX)

or salt, hydrate, or tautomer thereof, or combination thereof,
acetone,
water, and
aqueous ammonium hydroxide.

[119] A process for preparing a compound (Ic):

(Ic)

or a salt, hydrate, or any combination thereof, wherein the process comprises adding solvent (e.g., DMF) to the vessel containing compound (Ia):

(Ia)

or a salt, hydrate, or any combination thereof, and compound (Ib):

(Ib)

or a salt, hydrate, or any combination thereof;

stirring the mixture at a temperature in a range between about 15° C. and about 30° C. for about 5 minutes;

heating the mixture to between about 80° C. and about 120° C. and stirring the mixture for about 2 hours;

discharging the reaction mixture from the vessel to a clean, dry drum.

[120] A process for preparing a compound (Ie):

(Ie)

or a salt, hydrate, or any combination thereof, wherein the process comprises adding compound (Id):

(Id)

or a salt, hydrate, or any combination thereof to a vessel;

adding water to the vessel and agitating the vessel in a range between about 15° C. and about 30° C.;

adding $K_2CO_3$ aqueous solution to the vessel;

adding compound (Ic) to the vessel; aging the mixture in a range between about 15° C. and about 40° C. for about 2-4 hours.

[121] A process for preparing a compound, which is 3-(1-(4-methoxybenzyl)-5-methyl-1H-pyrazol-4-yl)-3-oxo-propanenitrile, represented as Compound (I):

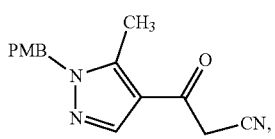

(I)

or a salt, hydrate, or any combination thereof, wherein the process comprises
reacting compound (Ie);

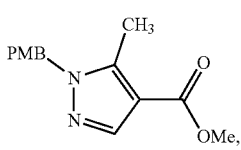

(Ie)

or a salt, hydrate, or any combination thereof, with MeCN under a nitrogen atmosphere.

EXAMPLES

Abbreviations

AcOH acetic acid
CDI 1,1-carbonyldiimidazole
DMF N,N-dimethylformamide
DMAc N,N-dimethylacetamide
DMSO dimethyl sulfoxide
(+)DBTA (2S,3S)-2,3-bis(benzoyloxy)butanedioic acid
(−)DBTA (2R,3R)-2,3-bis(benzoyloxy)butanedioic acid
EtOAc ethyl acetate
EtOH ethanol
MeCN acetonitrile
MeOH methanol
1-BuOH 1-butanol
2-BuOH 2-butanol
THF tetrahydrofuran
hr hours
min minutes
NMR nuclear magnetic resonance
% ee enantiomeric excess %

General Methods

Proton Nuclear Magnetic Resonance ($^1$H-NMR). Proton nuclear magnetic resonance ($^1$H-NMR) spectra were obtained on either a Bruker AVANCE 500 spectrometer at 500 MHz or a Bruker AVANCE 300 spectrometer at 300 MHz. Tetramethylsilane was used as an internal reference for proton spectra.

Example 1

Preparation of (2S,3S)-2,3-bis(benzoyloxy)butanedioic acid 2-[(2S)-1-azabicyclo[2.2.2]oct-2-yl]-6-(3-methyl-1H-pyrazol-4-yl)thieno[3,2-d]pyrimidin-4(3B)-one (1:1) (Compound (IX))

(+)DBTA.H$_2$O (42.1 kg) was dissolved in 1-butanol (133.7 L) at 20-30° C. to prepare a (+)DBTA solution. 2-(1-azabicyclo[2.2.2]oct-2-yl)-6-(3-methyl-1H-pyrazol-4-yl)thieno[3,2-d]pyrimidin-4(3H)-one (19.1 kg) was dissolved in 1-butanol (76.4 L) and acetic acid (76.4 L). Then, the mixture was heated to 80-90° C. The (+)DBTA solution prepared above was added dropwise followed by 1-butanol (19.1 L) at the same temperature. After dropwise addition, the mixture was stirred at the same temperature for 3 hrs. After confirmation of precipitation, a part of the solids was collected by filtration. As a result of chiral HPLC measurements, >75.0% ee was confirmed. After confirmation of >75.0% ee, ethyl acetate (152.8 L) was added dropwise at the same temperature. After dropwise addition, the mixture was stirred at the same temperature for 1 hr. The mixture was allowed to cool to 20-30° C. and stirred at the same temperature for 1 hr. After stirring, the crystals were collected by filtration and washed with ethyl acetate (95.5 L) to give wet crystals. The obtained wet crystals were dried under reduced pressure at 60° C. to give (2S,3S)-2,3-bis(benzoyloxy)butanedioic acid 2-[(2S)-1-azabicyclo[2.2.2]oct-2-yl]-6-(3-methyl-1H-pyrazol-4-yl)thieno[3,2-d]pyrimidin-4(3H)-one (1:1) as crystals (37.1 kg, yield 94.8%). Chiral HPLC showed the obtained product was 84.7% ee. Chiral HPLC Method: Column: CHIRALPAK® AD-H, 4.6×250 mm, 5 μm; Mobile Phase: n-hexane:2-propanol:diethylamine=600:400:1(v/v/v), Flow rate: 1.0 mL/min for 15 min.

Example 2

Diastereomeric Salt Resolution of 2-(1-Azabicyclo[2.2.2]Oct-2-yl)-6-(3-Methyl-1H-Pyrazol-4-yl)Thieno[3,2-d]Pyrimidin-4 (3B)-One from Various Chiral Acids Diastereomeric salt resolution of 2-(1-azabicyclo[2.2.2]oct-2-yl)-6-(3-methyl-1H-pyrazol-4-yl)thieno[3,2-d]pyrimidin-4(3H)-one was investigated by using various chiral acids. As shown in Table 1, 2-(1-azabicyclo[2.2.2]oct-2-yl)-6-(3-methyl-1H-pyrazol-4-yl)thieno[3,2-d]pyrimidin-4 (3H)-one formed diastereomeric salts with 6 chiral acids out of a total of 98 chiral acids tested in 2,2,2-trifluoroethanol, MeOH, MeOH/EtOH, or EtOH as the solvent. Optical purity was determined by chiral HPLC. Crystals obtained from (−)DBTA and N-Tosyl-D-valine showed good optical purity. Chiral HPLC Method: Column: CHIRALPAK® AD-H, 4.6×250 mm, 5 μm; Mobile Phase: n-hexane:2-propanol:diethylamine=600:400:1 (v/v/v), Flow rate: 1.0 mL/min for 15 min.

TABLE 1

Summary of diastereomeric salt resolution study 1

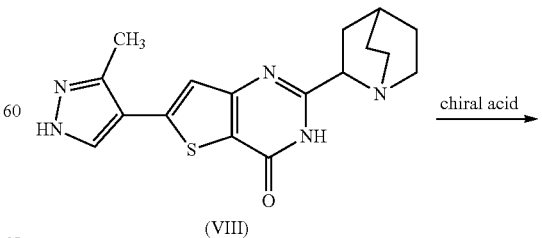

TABLE 1-continued (VIII) (chiral acid salt) • chiral acid

| Entry | Chiral acids (1 eq) | Solvents | Optical purity (% ee) | Yield (%) |
|---|---|---|---|---|
| 1 | (−)DBTA | MeOH | 36.3 (R form) | 33 |
| 2 | N-Tosyl-D-valine | MeOH/EtOH (1/1) | 62.9 (S form) | 12 |
| 3 | (R)-(+)-Malic acid | EtOH | 3.2 (R form) | N/A |
| 4 | (S)-(−)-Methyl succinic acid | EtOH | Racemate | N/A |
| 5 | N-Tosyl-L-phenylalanine | EtOH | Racemate | N/A |
| 6 | (S)-(+)-Mandelic acid | EtOH | Racemate | N/A |

Example 3

Dynamic Resolution of Diastereomeric Salt by Using 2-(1-Azabicyclo[2.2.2]Oct-2-yl)-6-(3-Methyl-1H-Pyrazol-4-yl) Thieno[3,2-d]Pyrimidin-4 (3H)-One with (+)DBTA.H$_2$O As shown in Table 2, diastereomeric salt resolution of 2-(1-azabicyclo[2.2.2]oct-2-yl)-6-(3-methyl-1H-pyrazol-4-yl)thieno[3,2-d]pyrimidin-4(3H)-one with (2S,3S)-2,3-bis(benzoyloxy)butanedioic acid monohydrate ((+)DBTA.H$_2$O) was investigated in MeOH or EtOH as the solvent. Dynamic resolution of diastereomeric salt was confirmed in MeOH as shown in entry 2. Addition of acetic acid accelerated the dynamic resolution as shown in entries 3 and 4. Chiral HPLC Method: Column: CHIRALPAK® AD-H, 4.6×250 mm, 5 μm; Mobile Phase: n-hexane:2-propanol:diethylamine=600:400:1(v/v/v), Flow rate: 1.0 mL/min for 15 min.

As shown in FIG. 1, 1-BuOH as the solvent was more effective than EtOH when the ratio of acetic acid was one third against 1-BuOH.

TABLE 2

Summary of dynamic resolution study using (+)DBTA•H$_2$O conditions (VIII) + (+)DBTA•H$_2$O → conditions → (IX)

| Entry | Conditions | Optical purity (% ee) | Yield (%) |
|---|---|---|---|
| 1 | MeOH (30 vol), 60° C., 22 h | 51.5 | 31 |
| 2 | MeOH (21 vol), 60° C., 22 h | 65.7 | 54 |
| 3 | MeOH/AcOH (50/1, 20 vol), 60° C., 22 h | 74.3 | 52 |
| 4 | EtOH/AcOH (10/1, 20 vol), 80° C., 28 h | 87.4 | 86 |

Example 4

Preparation of 2-[(2S)-1-Azabicyclo[2.2.2]Oct-2-yl]-6-(3-Methyl-1H-Pyrazol-4-yl)Thieno[3,2-d]Pyrimidin-4(3H)-One Hemihydrate (Compound (X))

(2S,3S)-2,3-bis(benzoyloxy)butanedioic acid 2-((2S)-1-azabicyclo[2.2.2]oct-2-yl)-6-(3-methyl-1H-pyrazol-4-yl)thieno[3,2-d]pyrimidin-4(3H)-one (1:1) (37.0 kg) was dissolved in acetone (74 L) and water (148 L) at 0-10° C. 25% aqueous ammonium hydroxide solution (9.9 L) was added dropwise at the same temperature. After dropwise addition, the mixture was stirred at the same temperature for 1 hr. Acetone (222 L) was added dropwise at the same temperature. After dropwise addition, the mixture was stirred at 20-30° C. for 1 hr. After stirring, the crystals were collected by filtration and washed with water (111 L), water (111 L) and acetone (74 L) successively to give wet crystals. The obtained wet crystals were dried under reduced pressure at 60° C. to give 2-[(2S)-1-azabicyclo[2.2.2]oct-2-yl]-6-(3-methyl-1H-pyrazol-4-yl)thieno[3,2-d]pyrimidin-4(3H)-one hemihydrate as crystals (13.1 kg, yield 72.6%). Chiral HPLC showed 91.0% ee. Chiral HPLC Method: Column: CHIRALPAK® AD-H, 4.6×250 mm, 5 μm; Mobile Phase: n-hexane:2-propanol:diethylamine=600:400:1(v/v/v), Flow rate: 1.0 mL/min for 15 min.

Example 5-1

Preparation of 2-(1-azabicyclo[2.2.2]oct-2-yl)-6-(3-methyl-1H-pyrazol-4-yl)thieno[3,2-d]pyrimidin-4(3M-one dihydrochloride (Compound (VII))

2-(1-azabicyclo[2.2.2]oct-2-yl)-6-[1-(4-methoxybenzyl)-5-methyl-1H-pyrazol-4-yl]thieno[3,2-d]pyrimidin-4(3H)-one(32.5 kg) was dissolved in acetic acid (65 L) at 20-30° C. Methanesulfonic acid (65 L) and anisole (7.6 kg) was added dropwise below 60° C. After dropwise addition, the mixture was stirred at 105-115° C. for 2 hrs. The mixture was allowed to cool to 40-60° C. Acetonitrile (162.5 L), ethanol (162.5 L) and concentrated hydrochloric acid (32.5 L) were added dropwise successively at the same temperature and stirred at 45-55° C. for 30 min. After confirmation of the precipitation of the crystals, concentrated hydrochloric acid (65 L) was added dropwise at 40-60° C. The mixture was allowed to cool to 20-30° C. and stirred for 1 hr. After stirring, the crystals were collected by filtration and washed with acetonitrile (162.5 L) to give wet crystals. The obtained wet crystals were dried under reduced pressure at 60° C. to give 2-(1-azabicyclo[2.2.2]oct-2-yl)-6-(3-methyl-1H-pyrazol-4-yl)thieno[3,2-d]pyrimidin-4(3H)-one dihydrochloride as crystals (28.3 kg, yield 97.0%).

Example 5-2

Preparation of 2-(1-azabicyclo[2.2.2]oct-2-yl)-6-(3-methylpyrazol-4-yl)thieno[3,2-d]pyrimidin-4(311)-one (Compound (VIII))

Potassium carbonate (11.3 kg) was dissolved in water (141.5 L) at 20-30° C. to prepare a potassium carbonate solution. 2-(1-azabicyclo[2.2.2]oct-2-yl)-6-(3-methyl-1H-pyrazol-4-yl)thieno[3,2-d]pyrimidin-4(3H)-one dihydrochloride (28.3 kg) was dissolved in water (424.5 L) and the mixture was heated to 75-85° C. The potassium carbonate solution prepared above was added dropwise at the same temperature. After dropwise addition, the mixture was stirred at the same temperature for 1 hr. The mixture was allowed to cool to 20-30° C. and stirred for 1 hr. After stirring, the crystals were collected by filtration and washed with water (141.5 L), water (141.5 L) and acetone (70.8 L) successively to give wet crystals. The obtained wet crystals were dried under reduced pressure at 60° C. to give 2-(1-azabicyclo[2.2.2]oct-2-yl)-6-(3-methyl-1H-pyrazol-4-yl)thieno[3,2-d]pyrimidin-4(3H)-one as crystals (19.1 kg, yield 81.9%).

Example 6

Deprotection of p-Methoxybenzyl Protecting Group by Various Conditions

Deprotection of p-methoxybenzyl protecting group (PMB) was investigated by using various conditions. As shown in Table 4, acidic conditions (trifluoroacetic acid (TFA), HCl, methanesulfonic acid (MsOH)) were effective for the deprotection. Especially a mixture of methanesulfonic acid and acetic acid resulted in short reaction time with high conversion rate as shown in Table 4.

TABLE 4

Summary of p-methoxybenzyl deprotection study

| Entry | Conditions | Conv. % |
|---|---|---|
| 1 | TFA (4 vol.), anisole (1 equiv.), reflux - 15 h | 99 |
| 2 | 10% Pd/C, H$_2$ (8 MPa), MeOH, 60° C. | 0 |
| 3 | 2,3-Dichloro-5,6-dicyano-1,4-benzoquinone (DDQ) (5 equiv.), THF, r.t. | 0 |
| 4 | Ceric ammonium nitrate (CAN) (5 equiv.), MeCN—H$_2$O, r.t. | 0 |
| 5 | NaH (6 equiv.), DMF, r.t. | 0 |
| 6 | AlCl$_3$ (2.5 equiv.), toluene, 100° C. - 1 h | 0.1 |
| 7 | SnCl$_2$•2H$_2$O (4 equiv.), c.HCl:EtOH (1:2), 100° C. - 17 h | 27 |
| 8 | 6M HCl (10 vol.), 100° C. - 24 h | 82 |
| 9 | c.HCl:AcOH (1:1) (10 vol.), anisole (1 equiv.), 100° C. - 24 h | 94 |
| 10 | c.HCl (10 vol.), 100° C. - 24 h | 97 |
| 11 | MsOH (2 vol.), anisole (1 equiv.), 100° C. - 8 h | 97 |
| 12 | MsOH:AcOH (1:1) (4 vol.), anisole (1 equiv.), 110° C. - 3 h | 98 |

Example 7

Preparation of Methyl 3-Amino-5-[1-(4-Methoxybenzyl)-5-Methyl-1H-Pyrazol-4-yl]Thiophene-2-Carboxylate (Compound (IV))

3-(1-(4-methoxybenzyl)-5-methyl-1H-pyrazol-4-yl)-3-oxopropanenitrile, (50.0 g, 185.7 mmol) and p-toluenesulfonic anhydride (64.6 g, 197.9 mmol) were dissolved in anhydrous THF (300 mL). Triethylamine (36.5 mL, 261.7 mmol) was added dropwise, keeping the temperature of the reaction mixture less than 25° C. The reaction mixture was stirred at 25° C. for 1 hour. Upon complete formation of p-toluenesulfonate intermediate, a solution of KOH (41.1 g, 732.6 mmol) in water (50 mL) was added, keeping the temperature of the reaction mixture less than 25° C. The reaction mixture was stirred at 25° C. for 1 hour. Upon complete formation of alkyne intermediate, saturated aqueous ammonium chloride (5.3 M, 72 mL) was added while maintaining a reaction temperature of 25° C. Methyl thioglycolate (13.6 g, 204.3 mmol) was added to the reaction mixture. The reaction mixture was stirred for 1 h at 25° C. After the alkyne intermediate was consumed, DBU (36.7 g, 241.4 mmol) was added to the reaction mixture. The reaction mixture was stirred for 1 hour at 25° C. Upon complete formation of the desired product, water (300 mL) was added over 30 minutes. Seed crystal of methyl 3-amino-5-[1-(4-methoxybenzyl)-5-methyl-1H-pyrazol-4-yl]thiophene-2-carboxylate (1.0 wt %, 0.50 g) was added to the reaction mixture. More water (450 mL) was added over 3 hours, and resulted in a suspension. The suspension was stirred at 25° C. for 3 hours. Methyl 3-amino-5-[1-(4-methoxybenzyl)-5-methyl-1H-pyrazol-4-yl]thiophene-2-carboxylate (53.0 g, 85% yield) was isolated via vacuum filtration, washed with THF/H$_2$O and then dried under vacuum, with a nitrogen bleed at 35° C. NMR data of compound (IV) which obtained through the same method mentioned above is described as follows; $^1$H-NMR(500 MHz, DMSO-d$_6$): δ 2.38(s, 3H), 3.70(s, 3H), 3.72(s, 3H), 5.28(s, 2H), 6.51(s, 2H), 6.54(s, 1H), 6.89(d, J=8.75 Hz, 2H), 7.13(d, J=8.75 Hz, 2H), 7.71(s, 1H).

Example 8

Preparation of methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate (Compound (V))

Quinuclidine-2-carboxylic acid hydrochloride (82.7 g, 431 mmol) was suspended in the mixture of MeCN (1.7 L), DMF (34 mL) and oxalyl chloride (37 mL). The reaction mixture was heated at 30-40° C. for 4 h to complete quinuclidine-2-carbonyl chloride formation which resulted in a thin suspension. After cooling to room temperature, methyl 3-amino-5-[1-(4-methoxybenzyl)-5-methyl-1H-pyrazol-4-yl]thiophene-2-carboxylate (140 g, mmol) was added. The reaction mixture was stirred at room temperature for 14 hours. HPLC analysis showed complete conversion to methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate. Water (1.1 L) was added. The pH of the reaction mixture was brought to 7.0 by slow addition of a solution of NaHCO$_3$ (114 g in 2.8 L of water). Precipitation formed. Methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate(171.1 g, 88.0%) was isolated via vacuum filtration, washed with 4/1 water/MeCN (400 mL) three times and then dried under vacuum, with a nitrogen bleed at 55° C.

Example 8'

Preparation of methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate (Compound (V))

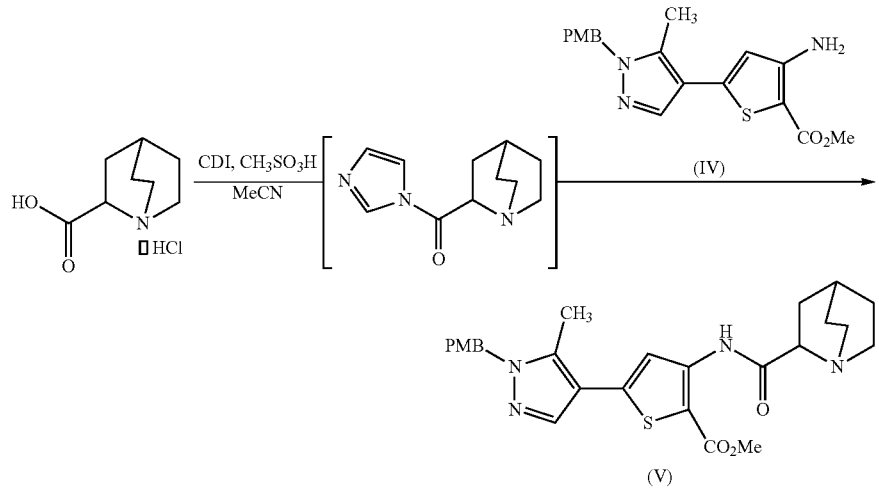

Quinuclidine-2-carboxylic acid hydrochloride (262 g, 1.365 mol) and CDI (289 g, 1.779 mol) were suspended in an anhydrous MeCN (2.4 L) in a reactor (1). The reaction mixture was heated at 35-40° C. for 3 hr to complete (1H-imidazol-1-yl) (quinuclidin-2-yl)methanone hydrochloride formation. After cooling to room temperature, methanesulfonic acid (1.119 Kg, 11.639 mol) was slowly charged to the reaction mixture. The resultant solution was heated for 30 minutes to complete protonation of the intermediate.

In a separate reactor (2), methyl 3-amino-5-[1-(4-methoxybenzyl)-5-methyl-1H-pyrazol-4-yl]thiophene-2-carboxylate (400 g, 1.119 mol) was suspended in an anhydrous MeCN (2.4 L). The reaction mixture from reactor (1) was slowly transferred to the reactor (2). Reactor (1) was rinsed with an anhydrous MeCN (0.8 L). Rinse was transferred to the reactor (2). Reaction mixture was stirred at 20° C. for 12 hours. HPLC analysis showed complete conversion to methyl 5-(1-(4-methoxybenzyl)-5-methyl-1H-pyrazol-4-yl)-3-(quinuclidine-2-carboxamido)thiophene-2-carboxylate. Water (1.2 L) was slowly added to the batch. Reaction mixture was heated to 45-50° C.

The pH of the reaction mixture was brought to 5.97 by slow addition of a solution of K$_2$CO$_3$ (697 g in 1.2 L of water). Aqueous layer was separated. The pH of the organic layer was brought to 8.05 by slow addition of a solution of KHCO$_3$ (202 g in 4.8 L of water). Precipitation formed. The suspension was stirred for 1 h, cooled to 20° C., and then stirred for 1 h. Methyl 5-(1-(4-methoxybenzyl)-5-methyl-1H-pyrazol-4-yl)-3-(quinuclidine-2-carboxamido)thiophene-2-carboxylate (525 g, 94.7%) was isolated via vacuum filtration, washed with 5.66/1 water/MeCN (2 L) two times and then dried under vacuum at 50° C.

NMR data of compound (V) which obtained through the same method mentioned above is described as follows;

¹H-NMR(500 MHz, DMSO-d₆): δ 1.40(m, 2H), 1.50(m, 2H), 1.81(m, 3H), 2.43(s, 3H), 2.63(m, 1H), 2.78(m, 1H), 2.91(m, 1H), 3.02(m, 1H), 3.59(t, J=8.82, 8.82 Hz, 1H), 3.72(s, 3H), 3.80(s, 3H), 5.30(s, 2H), 6.89(d, J=8.75 Hz, 2H), 7.15(d, J=8.75 Hz, 2H), 7.81(s, 1H), 8.11(s, 1H), 11.2(s, 1H).

Example 9

Preparation of 2-(1-Azabicyclo[2.2.2]Oct-2-yl)-6-[1-(4-Methoxybenzyl)-5-Methyl-1H-Pyrazol-4-yl] Thieno[3,2-d]Pyrimidin-4(3H)-One (Compound (VI))

Methyl 3-[(1-azabicyclo[2.2.2]oct-2-ylcarbonyl)amino]-5-[1-(4-methoxybenzyl)-5-methyl-1H-pyrazol-4-yl]thiophene-2-carboxylate (120 g, 243 mmol) was suspended in formamide (480 mL). DMAc (720 mL) was added, followed by charging of potassium tert-butoxide (134 g, 1.2 mol). The reaction mixture was heated at 70° C. for 1 h; complete conversion to 2-(1-azabicyclo[2.2.2]oct-2-yl)-6-[1-(4-methoxybenzyl)-5-methyl-1H-pyrazol-4-yl]thieno[3,2-d] pyrimidin-4(3H)-one was obtained. The reaction mixture was cooled to 55° C. Water (2.4 L) was added and the temperature was kept at 55° C. The pH of the reaction mixture was adjusted to 10 by slowly adding HCl solution (¼ conc. HCl/water). 2-(1-Azabicyclo[2.2.2]oct-2-yl)-6-[1-(4-methoxybenzyl)-5-methyl-1H-pyrazol-4-yl]thieno[3,2-d]pyrimidin-4(3H)-one was precipitated. The suspension was stirred at 55° C. for 10 minutes, and then was cooled to room temperature in 1 hour. 2-(1-Azabicyclo[2.2.2]oct-2-yl)-6-[1-(4-methoxybenzyl)-5-methyl-1H-pyrazol-4-yl]thieno[3,2-d]pyrimidin-4(3H)-one (92.0 g, 82.0%) was isolated via vacuum filtration, washed with water (2×1.2 L), and then dried under vacuum, with a nitrogen bleed at 55° C.

NMR data of compound (VI) which obtained through the same method mentioned above is described as follows; ¹H-NMR(300 MHz, DMSO-d₆): δ 1.43(m, 2H), 1.50(m, 2H), 1.73(m, 1H), 1.85(s, 1H), 2.26(m, 1H), 2.47(s, 3H), 2.57(m, 2H), 2.84(m, 1H), 3.07(m, 1H), 3.72(s, 3H), 3.90(t, J=8.72, 8.72 Hz, 1H), 5.32(s, 2H), 6.91(d, J=8.74 Hz, 2H), 7.17(d, J=8.74 Hz, 2H), 7.45(s, 1H), 7.92(s, 1H), 11.6(s, 1H).

Example 10

Preparation of 2-(1-Azabicyclo[2.2.2]Oct-2-yl)-6-(3-Methyl-1H-Pyrazol-4-yl)Thieno[3,2-d]Pyrimidin-4 (3H)-One (Compound (VIII))

To 2-(1-azabicyclo[2.2.2]oct-2-yl)-6-[1-(4-methoxybenzyl)-5-methyl-1H-pyrazol-4-yl]thieno[3,2-d]pyrimidin-4 (3H)-one (18 Kg, 39.0 mol) was added acetic acid (36 L), followed by methanesulfonic acid (36 L) at <50° C. Anisole (4.3 L) was added. The reaction mixture was heated to 105-115° C. and then maintained for >2 h. After complete deprotection, the reaction mixture was cooled to 40-60° C. MeCN (90 L) was added, followed by addition of EtOH (90 L). Conc. HCl (18 L) was added, and the reaction mixture was stirred at 50° C. for 30 minutes. Precipitation of 2-(1-azabicyclo[2.2.2]oct-2-yl)-6-(3-methyl-1H-pyrazol-4-yl)thieno[3,2-d]pyrimidin-4(3H)-one dihydrochloride was observed. The suspension was stirred for 1 h at 50° C. More conc. HCl (36 L) was added at 50° C. The suspension was cooled to room temperature in 1 h, and then stirred for >1 h. The solids of 2-(1-azabicyclo[2.2.2]oct-2-yl)-6-(3-methyl-1H-pyrazol-4-yl)thieno[3,2-d]pyrimidin-4(3H)-one dihydrochloride were filtered, and then washed with MeCN (2×90 L). The solids were dried at 60° C. under vacuum for >3 h to afford 15.6 Kg of 2-(1-azabicyclo[2.2.2]oct-2-yl)-6-(3-methyl-1H-pyrazol-4-yl)thieno[3,2-d]pyrimidin-4 (3H)-one dihydrochloride. 2-(1-azabicyclo[2.2.2]oct-2-yl)-6-(3-methyl-1H-pyrazol-4-yl)thieno[3,2-d]pyrimidin-4 (3H)-one dihydrochloride was stirred in water (243 L) and heated to 80° C. A solution of K₂CO₃ (6.5 Kg) in water (81 L) was slowly added during 1 h. 2-(1-azabicyclo[2.2.2]oct-2-yl)-6-(3-methyl-1H-pyrazol-4-yl)thieno[3,2-d]pyrimidin-4(3H)-one was precipitated. The suspension was stirred at 80° C. for 1 hour, and then cooled to room temperature in 1 h. After stirring at room temperature for >1 hour, solids were filtered, and then washed with water (2×81 L), and then MeCN (41 L). 2-(1-azabicyclo[2.2.2]oct-2-yl)-6-(3-methyl-1H-pyrazol-4-yl)thieno[3,2-d]pyrimidin-4(3H)-one (11.8 kg, 88.6%) was dried under vacuum, with a nitrogen bleed at 60° C.

NMR data of compound (VIII) which obtained through the same method mentioned above is described as follows; ¹H-NMR(300 MHz, DMSO-d₆): δ 1.43(m, 2H), 1.50(m, 2H), 1.73(m, 1H), 1.85(s, 1H), 2.26(m, 1H), 2.47(s, 3H), 2.57(m, 2H), 2.84(m, 1H), 3.07(m, 1H), 3.72(s, 3H), 3.90(t, J=8.72, 8.72 Hz, 1H), 5.32(s, 2H), 6.91(d, J=8.74 Hz, 2H), 7.17(d, J=8.74 Hz, 2H), 7.45(s, 1H), 7.92(s, 1H), 11.6(s, 1H).

Example 11

Preparation of (2S,3S)-2,3-bis(benzoyloxy)butanedioic acid 2-[(2S)-1-azabicyclo[2.2.2]oct-2-yl]-6-(3-Methyl-1H-pyrazol-4-yl)thieno[3,2-d]pyrimidin-4 (3B)-one (1:1) (Compound (IX))

To 2-(1-azabicyclo[2.2.2]oct-2-yl)-6-(3-methyl-1H-pyrazol-4-yl)thieno[3,2-d]pyrimidin-4(3H)-one (22.7 Kg) and (+)DBTA.H₂O (22.7 Kg), were added acetic acid (91 L) and 2-BuOH (91 L). The reaction mixture was heated to 80° C., resulted in a solution. A solution of (+)DBTA.H₂O (18.45 Kg) in 2-BuOH (182 L) was added at 85-90° C. The reaction mixture, a suspension, was stirred at 90° C. for 8 hours. Samples of the solids were analyzed every two hours until the diastereomeric excess reached >80%. The suspension was cooled to room temperature slowly, then stirred at room temperature for >1 hour. The solids were filtered, and then washed with EtOAc (2×91 L). (2S,3S)-2,3-bis(benzoyloxy) butanedioic acid 2-[(2S)-1-azabicyclo[2.2.2]oct-2-yl]-6-(3-methyl-1H-pyrazol-4-yl)thieno[3,2-d]pyrimidin-4(3H)-one (1:1) (37.9 kg, 81.5%) was dried under vacuum, with a nitrogen bleed at 60° C. ¹H-NMR(500 MHz, DMSO-d₆): δ 1.59-1.73(m, 4H), 2.03-2.23(m, 3H), 2.46(s, 3H), 2.99-3.31 (m, 4H), 4.40(t, J=9.1 Hz, 1H), 5.73(s, 2H), 7.43(s, 1H), 7.50-7.56(m, 4H), 7.64-7.68(m, 2H), 7.96(dd, J=8.2, 1.3 Hz, 4H), 8.07 (s, 1H). Anal. Calcd for C₃₅H₃₃N₅O₉S: C, 60.08; H, 4.75; N, 10.01. Found: C, 59.97; H, 4.69; N, 10.01. M.p. 196.4° C.

Example 11'

Preparation of (2S,3S)-2,3-bis(benzoyloxy)butanedioic acid 2-[(2S)-1-azabicyclo[2.2.2]oct-2-yl]-6-(3-methyl-1H-pyrazol-4-yl)thieno[3,2-d]pyrimidin-4 (3B)-one (1:1) (Compound (IX))

To 2-(1-azabicyclo[2.2.2]oct-2-yl)-6-(3-methyl-1H-pyrazol-4-yl)thieno[3,2-d]pyrimidin-4(3H)-one (22.4 Kg), was added acetic acid (90 L) and 2-BuOH (90 L). The reaction mixture was heated to 81-85° C., resulted in a solution. A solution of (+)DBTA.H₂O (50.0 Kg) in 2-BuOH (179 L) was added at 81-85° C. The reaction mixture, a suspension, was stirred at 84° C. for 27 hours. Samples of the solids were analyzed every two hours until the diastereomeric excess reached >80%. The suspension was cooled to room temperature slowly, then stirred at room temperature for >1 hour. The solids were filtered, and then washed with EtOAc (2×91 L). (2S,3S)-2,3-bis(benzoyloxy)butanedioic acid 2-[(2S)-1-azabicyclo[2.2.2]oct-2-yl]-6-(3-methyl-1H-pyrazol-4-yl)thieno[3,2-d]pyrimidin-4(3H)-one (1:1) (41.9 kg, 91.3%) was dried under vacuum, with a nitrogen bleed at 60° C. ¹H-NMR(500 MHz, DMSO-d₆): δ 1.59-1.73(m, 4H), 2.03-2.23(m, 3H), 2.46(s, 3H), 2.99-3.31(m, 4H), 4.40(t, J=9.1 Hz, 1H), 5.73(s, 2H), 7.43(s, 1H), 7.50-7.56(m, 4H), 7.64-7.68(m, 2H), 7.96(dd, J=8.2, 1.3 Hz, 4H), 8.07(s, 1H). Anal. Calcd for C₃₅H₃₃N₅O₉S: C, 60.08; H, 4.75; N, 10.01. Found: C, 59.97; H, 4.69; N, 10.01. M.p. 196.4° C.

Example 12

Preparation of 2-[(2S)-1-Azabicyclo[2.2.2]Oct-2-yl]-6-(3-Methypyrazol-4-yl)Thieno[3,2-d]Pyrimidin-4(3H)-One Hemihydrate (Compound (X))

(2S,3S)-2,3-bis(benzoyloxy)butanedioic acid 2-[(2S)-1-azabicyclo[2.2.2]oct-2-yl]-6-(3-methyl-1H-pyrazol-4-yl)thieno[3,2-d]pyrimidin-4(3H)-one (1:1) (37.9 Kg) was dissolved in DMSO (148 L). At <35° C., ammonia (~30% aqueous solution) was slowly charged until pH 8.5-9.0. The reaction mixture was heated to 50° C. A solution of 1/1 water/acetone (11 Kg) was added to the reaction mixture at 50° C. More 1/1 water/acetone (25 Kg) was added slowly to the reaction mixture at 50° C. The free base was precipitated. The suspension was cooled to room temperature in 1 hour, and then stirred for 2 h. The solids were filtrated and washed with 1/1 water/acetone (16 Kg) followed by acetone (19 L). The product (16 kg, 84.3%) was dried under vacuum, with a nitrogen bleed at 60° C. ¹H-NMR was identical to 2-[(2S)-1-azabicyclo[2.2.2]oct-2-yl]-6-(3-methyl-1H-pyrazol-4-yl)thieno[3,2-d]pyrimidin-4(3H)-one hemihydrate. Chiral HPLC showed 93% ee. Chiral HPLC Method: Column: CHIRALPAK® AD-H, 4.6×250 mm, 10 µm; Mobile Phase: 60:40:0.1% v/v, n-hexane:IPA:DEA; Flow rate: 1 mL/min for 15 min.

While the foregoing invention has been described in some detail for purposes of clarity and understanding, these particular embodiments are to be considered as illustrative and not restrictive. It will be appreciated by one skilled in the art from a reading of this specification that various changes in form and detail can be made without departing from the true scope of the invention, which is to be defined by the appended claims rather than by the specific embodiments. The patent and scientific literature referred to herein establishes knowledge that is available to those with skill in the art. Unless otherwise defined, all technical and scientific terms used herein have the same meaning as commonly understood by one of ordinary skill in the art to which this invention belongs. The issued patents, applications, and references that are cited herein are hereby incorporated by reference to the same extent as if each was specifically and individually indicated to be incorporated by reference. In the case of inconsistencies, the present specification, including definitions, will control.

The invention claimed is:

1. A process for preparing a compound, which is 2-[(2S)-1-azabicyclo[2.2.2]oct-2-yl]-6-(3-methyl-1H-pyrazol-4-yl)thieno[3,2-d]pyrimidin-4(3H)-one, represented as Compound (XI):

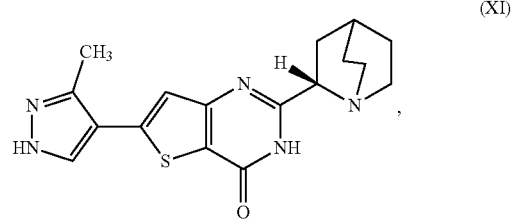 [SMILES: Cc1n[nH]cc1-c1cc2nc([C@@H]3CC4CCN3CC4)[nH]c(=O)c2s1]

(XI)

or a salt, hydrate, or tautomer thereof, or any combination thereof, the process comprising treating 2-(1-azabicyclo[2.2.2]oct-2-yl)-6-(3-methyl-1H-pyrazol-4-yl)thieno[3,2-d]pyrimidin-4(3H)-one, represented as Compound (VIII):

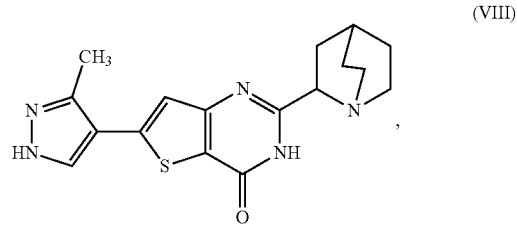 [SMILES: Cc1n[nH]cc1-c1cc2nc(C3CC4CCN3CC4)[nH]c(=O)c2s1]

(VIII)

or a salt, hydrate, or tautomer thereof, or any combination thereof, with a chiral acid in the presence of a dynamic resolution promoter to produce a chiral acid salt of 2-[(2S)-1-azabicyclo[2.2.2]oct-2-yl]-6-(3-methyl-1H-pyrazol-4-yl)thieno[3,2-d]pyrimidin-4(3H)-one, and treating the chiral acid salt of 2-[(2S)-1-azabicyclo[2.2.2]oct-2-yl]-6-(3-methyl-1H-pyrazol-4-yl)thieno[3,2-d]pyrimidin-4(3H)-one with a base to form the Compound (XI) or hydrate, or tautomer thereof, or combination thereof, wherein the chiral acid is at least one acid selected from the group consisting of:

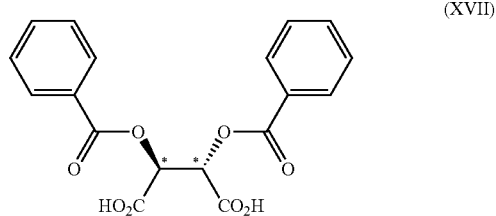 [SMILES: O=C(O[C@H](C(=O)O)[C@H](OC(=O)c1ccccc1)C(=O)O)c1ccccc1]

(XVII)

or a hydrate thereof; and

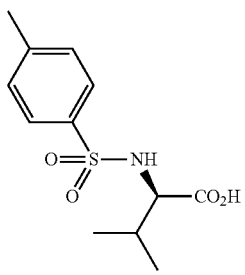

(XX)

or a hydrate thereof.

2. The process according to claim 1, wherein the dynamic resolution promoter comprises formic acid, acetic acid, propionic acid, trifluoroacetic acid, benzoic acid, triethylamine, 1,4-diazabicyclo[2.2.2]octane, or diazabicycloundecene.

3. The process according to claim 1, wherein the dynamic resolution promoter comprises acetic acid.

4. The process according to claim 1, wherein the treating of the 2-(1-azabicyclo[2.2.2]oct-2-yl)-6-(3-methyl-1H-pyrazol-4-yl)thieno[3,2-d]pyrimidin-4(3H)-one as the Compound (VIII), or salt, hydrate, or tautomer thereof, or combination thereof with the chiral acid in the presence of the dynamic resolution promoter is performed in the presence of a solvent.

5. The process according to claim 4, wherein the solvent comprises at least one material selected from the group consisting of water, toluene, heptane, tetrahydrofuran, $C_{1-6}$ aliphatic alcohol, and ethyl acetate.

6. The process according to claim 4, wherein the solvent comprises 1-butanol.

7. The process according to claim 4, wherein the solvent comprises 2-butanol.

8. The process according to claim 1, wherein the Compound (XI), or hydrate thereof or tautomer thereof, or combination thereof is Compound (XI) hemihydrate or a tautomer thereof, or any combination thereof.

9. The process according to claim 4, wherein the solvent comprises methanol.

10. The process according to claim 4, wherein the solvent comprises ethanol.

11. The process according to claim 4, wherein the solvent comprises methanol and the dynamic resolution promoter comprises acetic acid.

12. The process according to claim 4, wherein the solvent comprises ethanol and the dynamic resolution promoter comprises acetic acid.

* * * * *